US011979715B2

(12) United States Patent
Croghan et al.

(10) Patent No.: US 11,979,715 B2
(45) Date of Patent: *May 7, 2024

(54) MULTIPLE SOUND SOURCE ENCODING IN HEARING PROSTHESES

(71) Applicant: Cochlear Limited, Macquarie University (AU)

(72) Inventors: Naomi Croghan, Centennial, CO (US); Harish Krishnamoorthi, Centennial, CO (US); Zachary Mark Smith, Pymble (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/968,980

(22) Filed: Oct. 19, 2022

(65) Prior Publication Data

US 2023/0082528 A1 Mar. 16, 2023

Related U.S. Application Data

(63) Continuation of application No. 17/268,801, filed as application No. PCT/IB2019/059179 on Oct. 25, 2019, now Pat. No. 11,510,015.

(Continued)

(51) Int. Cl.
*H04R 25/00* (2006.01)
*A61N 1/05* (2006.01)
*A61N 1/36* (2006.01)

(52) U.S. Cl.
CPC ......... *H04R 25/356* (2013.01); *H04R 25/505* (2013.01); *H04R 25/604* (2013.01);

(Continued)

(58) Field of Classification Search
CPC .. H04R 25/356; H04R 25/609; H04R 25/505; H04R 25/604; H04R 25/602; H04R 2225/67; A61N 1/36038; A61N 1/0541
See application file for complete search history.

(56) References Cited

U.S. PATENT DOCUMENTS 7,231,257 B2 6/2007 McDermott et al.
8,605,923 B2 12/2013 Goorevich et al.
(Continued)

FOREIGN PATENT DOCUMENTS

JP 2001519127 A 10/2001
JP 2005531175 A 10/2005
JP 2012517124 A 7/2012

OTHER PUBLICATIONS

International Search Report and Written Opinion in counterpart International Application No. PCT/IB2019/059179, dated Jan. 31, 2020, 11 pages.

(Continued)

*Primary Examiner* — Mark Fischer
(74) *Attorney, Agent, or Firm* — Edell, Shapiro & Finnan, LLC

(57) ABSTRACT

Presented herein are techniques for enhancing a hearing prosthesis recipient's perception of multiple frequencies present in received sound signals. The hearing prosthesis is configured to extract a plurality of frequencies from the received sound signals and to use the plurality of frequencies to modulate the amplitudes of different stimulation pulse sequences that are to be delivered to the recipient via different stimulation channels. The hearing prosthesis may also adapt a stimulation resolution of the stimulation pulse sequences when delivering the modulated stimulation pulses sequences to the recipient.

20 Claims, 17 Drawing Sheets

Related U.S. Application Data

(60) Provisional application No. 62/754,608, filed on Nov. 2, 2018.

(52) U.S. Cl.
CPC .......... *H04R 25/609* (2019.05); *A61N 1/0541* (2013.01); *A61N 1/36038* (2017.08); *H04R 25/602* (2013.01); *H04R 2225/67* (2013.01)

(56) References Cited

U.S. PATENT DOCUMENTS

| | | | |
|---|---|---|---|
| 8,688,222 B2 | 4/2014 | Smith | |
| 8,914,124 B2 | 12/2014 | Litvak et al. | |
| 9,084,893 B2 | 7/2015 | Vandali et al. | |
| 9,131,324 B2 | 9/2015 | Goorevich et al. | |
| 9,240,193 B2 | 1/2016 | James | |
| 9,570,057 B2 | 2/2017 | Brown | |
| 9,744,357 B2 | 8/2017 | Goorevich et al. | |
| 11,510,015 B2* | 11/2022 | Croghan ................ | H03G 9/025 |
| 2005/0107843 A1* | 5/2005 | McDermott ....... | A61N 1/36038 607/57 |
| 2009/0187237 A1 | 7/2009 | Fridman et al. | |
| 2011/0286618 A1* | 11/2011 | Vandali .............. | A61N 1/36038 381/320 |
| 2015/0092967 A1* | 4/2015 | Fitz ...................... | H04R 25/356 381/317 |
| 2015/0328457 A1 | 11/2015 | Litvak et al. | |
| 2016/0184586 A1 | 6/2016 | Okuyama | |
| 2018/0140838 A1 | 5/2018 | Smith | |
| 2019/0070413 A1* | 3/2019 | Phillips .............. | A61N 1/37211 |

OTHER PUBLICATIONS

M. R. Every and J. E. Szymanski, "Separation of synchronous pitched notes by spectral filtering of harmonics," IEEE Transactions on Audio, Speech, and Language Processing, vol. 14, No. 5 (2006): 1845-1856.

P. Smaragdis and J. C. Brown, "Non-negative matrix factorization for polyphonic music transcription," in Proceedings of the 2001 IEEE Workshop on the Applications of Signal Processing to Audio and Acoustics (2003): 177-180.

T. Virtanen, "Monaural sound source separation by nonnegative matrix factorization with temporal continuity and sparseness criteria," IEEE Transactions on Audio, Speech, and Language Processing, vol. 15, No. 3 (2007): 1066-1074.

G. J. Brown and M. P. Cooke, "Perceptual grouping of musical sounds: A computational model," Journal of New Music Research, vol. 23 (1994): 107-132.

Y. Li and D. L. Wang, "Musical sound separation using pitch-based labeling and binary time-frequency masking," in Proceedings of the IEEE International Conference on Acoustics, Speech, and Signal Processing (2008): 173-176.

J. Salamon and E. Gómez, "Melody extraction from polyphonic music signals using pitch contour characteristics," IEEE Transactions on Audio, Speech, and Language Processing, vol. 20, No. 6 (2012): 1759-1770.

Y. Li, J. Woodruff and D.L. Wang, "Monaural musical sound separation based on pitch and common amplitude modulation," in IEEE Transactions on Audio, Speech, and Language Processing, vol. 17, No. 7 (2009): 1361-1371.

G. Hu and D. Wang, "Speech segregation based on pitch tracking and amplitude modulation," Proceedings of the 2001 IEEE Workshop on the Applications of Signal Processing to Audio and Acoustics (Cat. No.01TH8575), New Platz, NY (2001): 79-82.

T.-W. Lee, M. Lewicki, M. Girolami, and T. Sejnowski, "Blind source separation of more sources than mixtures using overcomplete representations," IEEE Signal Processing Letters, vol. 6, No. 4 (1999): 87-90.

O. Yilmaz and S. Rickard, "Blind separation of speech mixtures via time-frequency masking," IEEE Transactions on Signal Processing, vol. 52, No. 7 (2004): 1830-1847.

J. Le Roux, J. R. Hershey and F. Weninger, "Deep NMF for speech separation," 2015 IEEE International Conference on Acoustics, Speech and Signal Processing (ICASSP), South Brisbane, QLD (2015): 66-70.

A. Klapuri, "Multiple fundamental frequency estimation based on harmonicity and spectral smoothness," IEEE Transactions on Audio, Speech, and Language Processing, vol. 11, No. 6 (2003): 804-816.

M. Genussov and I. Cohen, "Multiple fundamental frequency estimation based on sparse representations in a structured dictionary," Digital Signal Processing, vol. 23, No. 1 (2013): 390-400.

T. Tolonen and M. Karjalainen, "A computationally efficient multipitch analysis model" IEEE Transactions on Speech and Audio Processing, vol. 8, No. 6 (2000): 708-716.

Z. Smith, W. Parkinson, and C. Long. "Multipolar current focusing increases spectral resolution in cochlear implants," Proceedings of the Annual International IEEE EMBS Conference (2013): 2796-2799.

\* cited by examiner

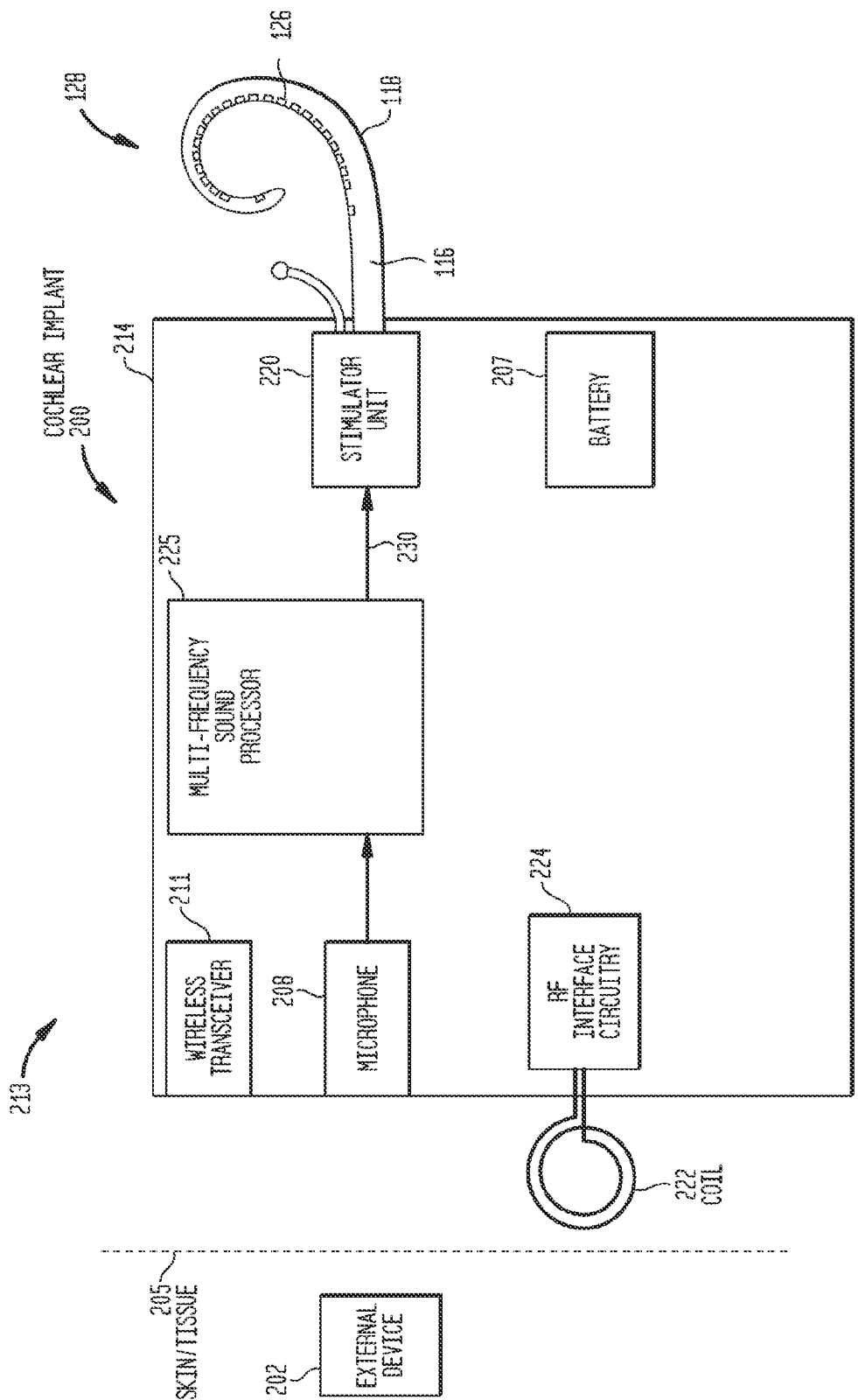

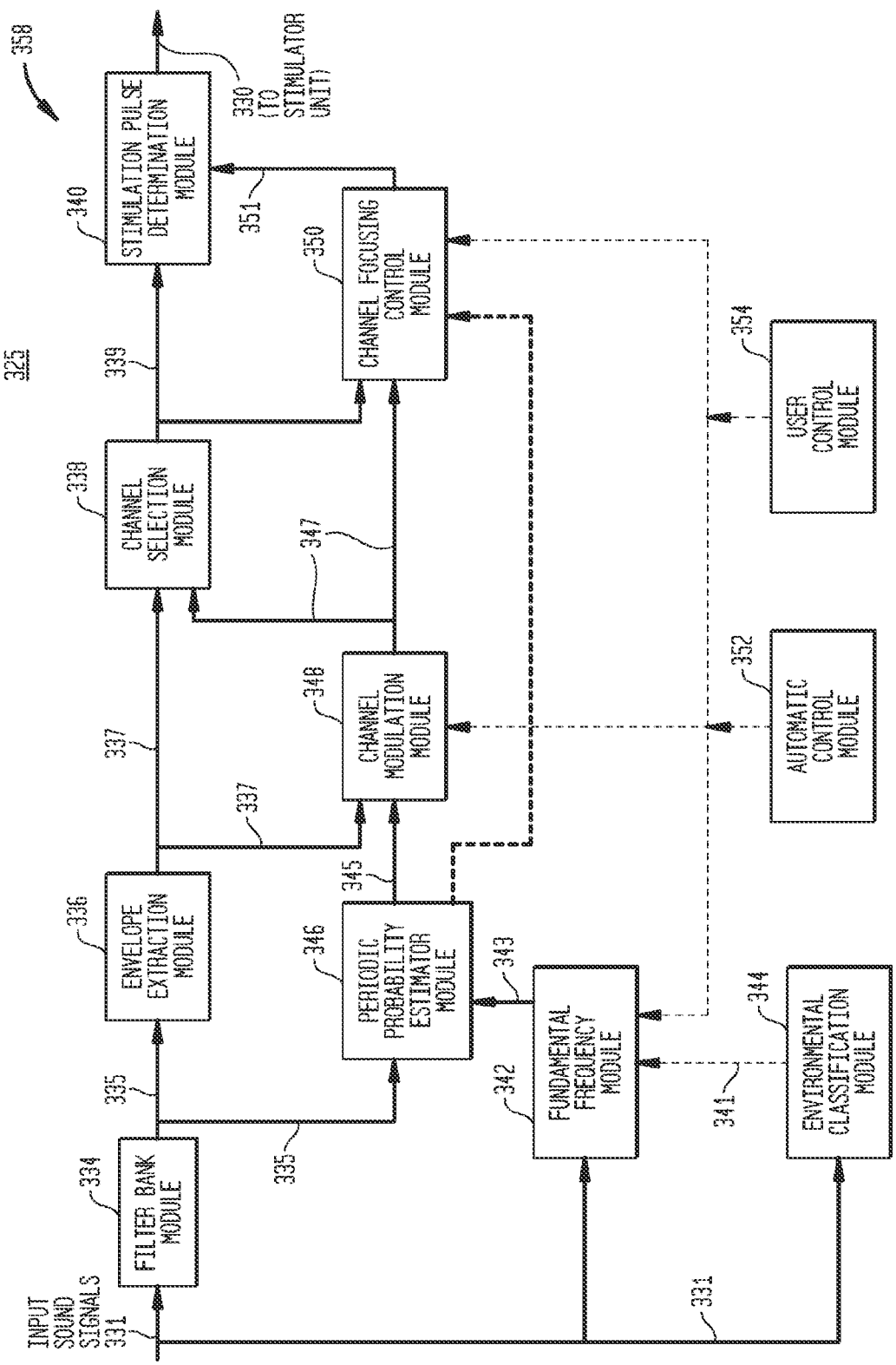

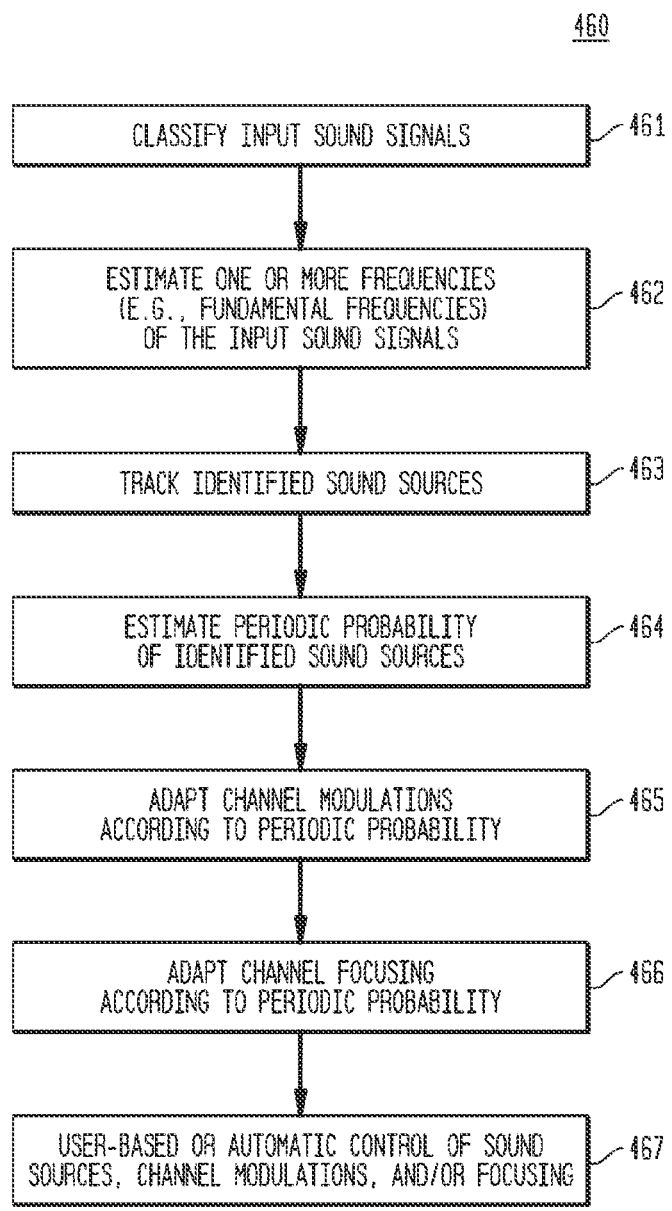

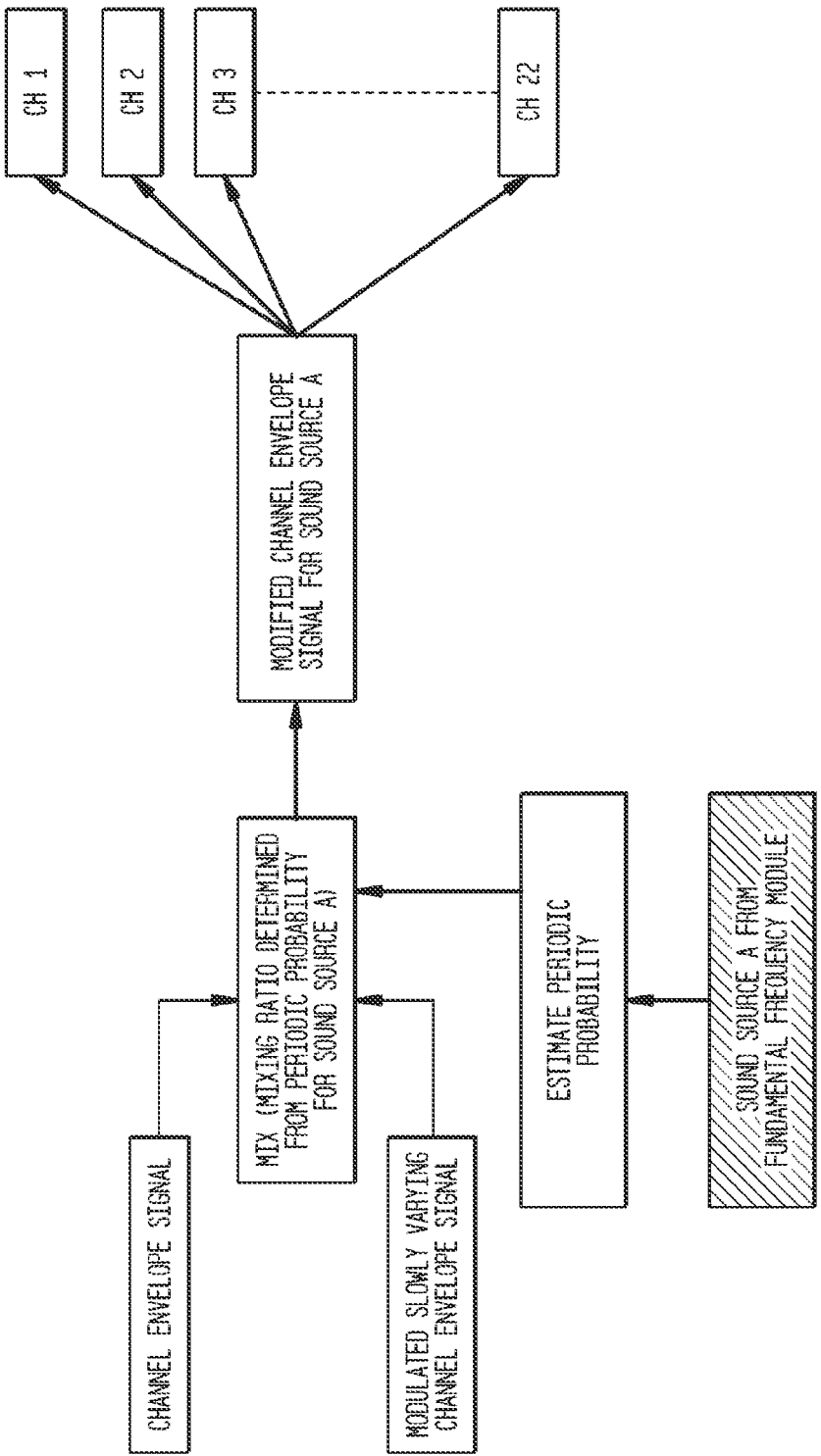

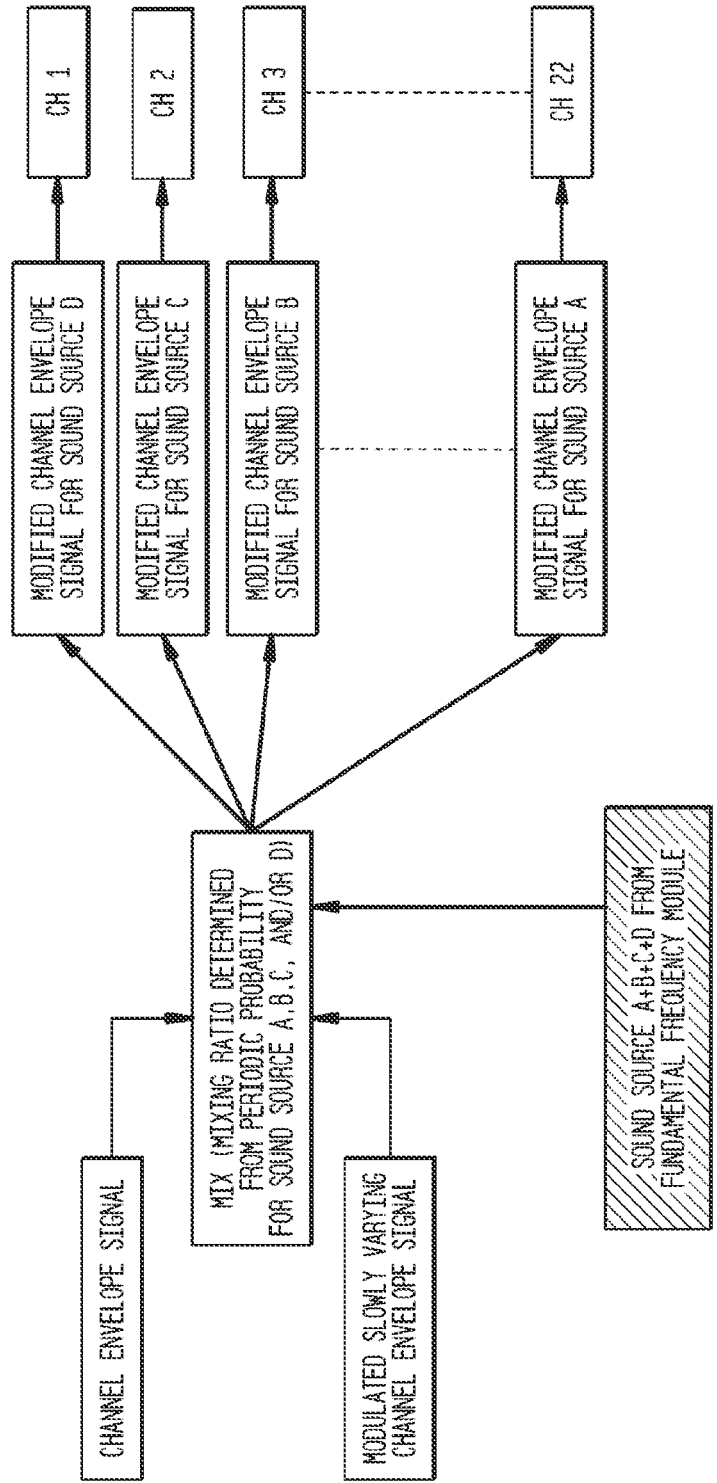

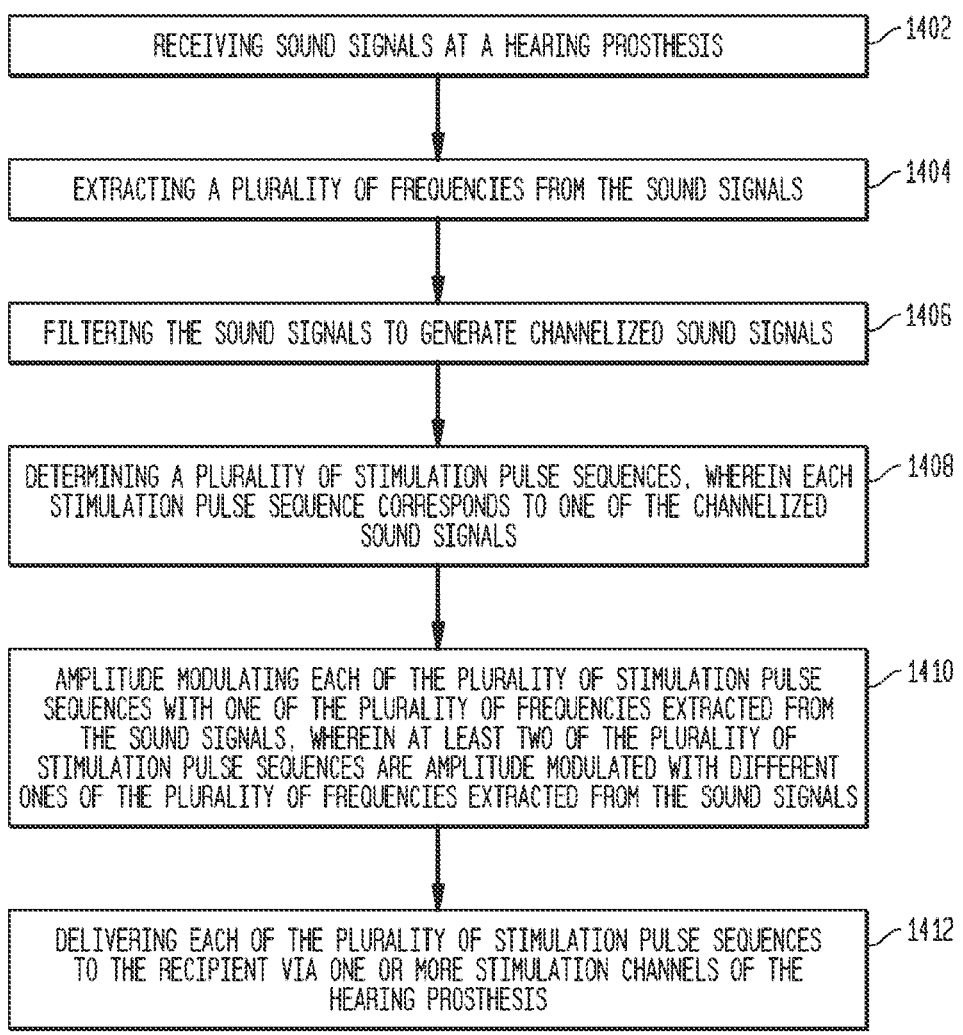

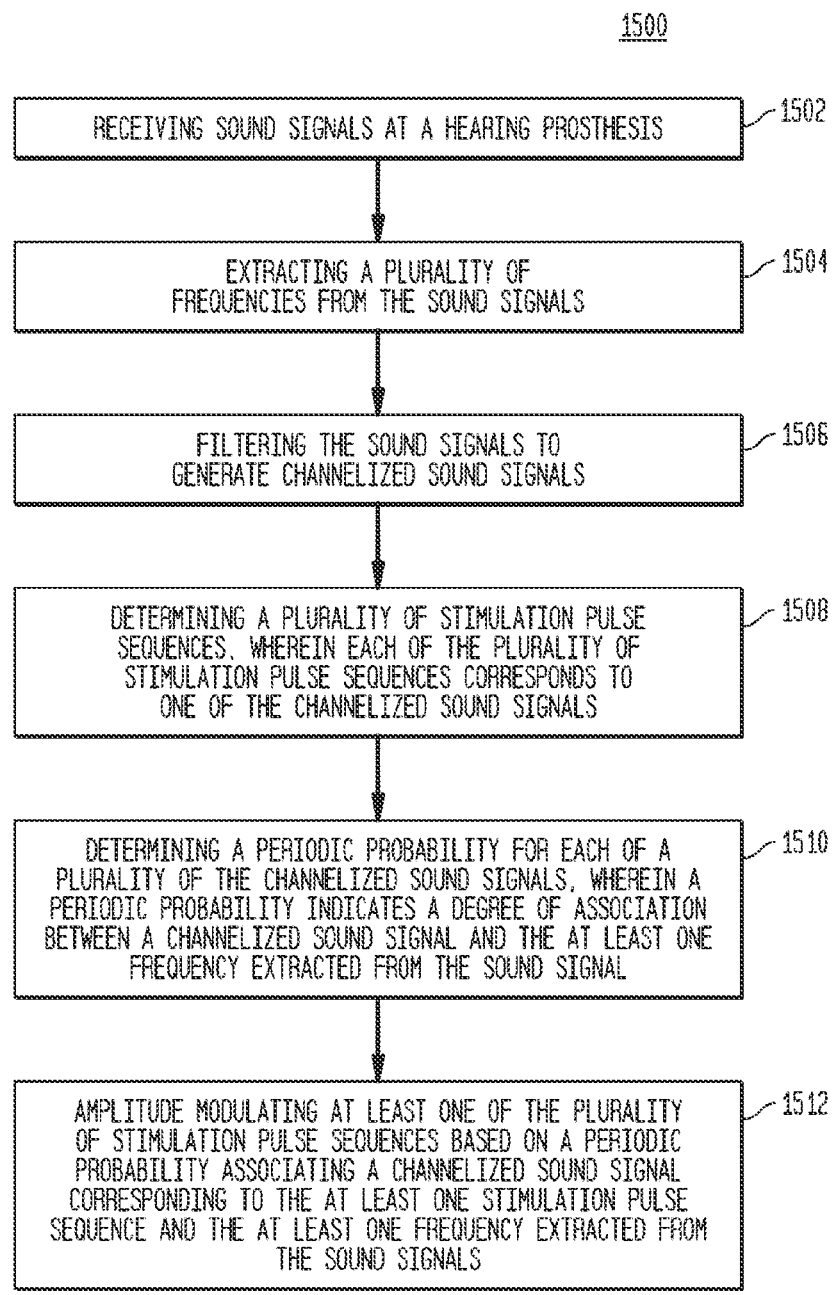

MULTIPLE SOUND SOURCE ENCODING IN HEARING PROSTHESES

BACKGROUND

Field of the Invention

The present invention relates generally to electrically-stimulating hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive a hearing prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating hearing prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: receiving sound signals at a hearing prosthesis; extracting a plurality of frequencies from the sound signals; filtering the sound signals to generate channelized sound signals; determining a plurality of stimulation pulse sequences, wherein each stimulation pulse sequences corresponds to one of the channelized sound signals; amplitude modulating each of the plurality of stimulation pulse sequences with one of the plurality of frequencies extracted from the sound signals, wherein at least two of the plurality of stimulation pulse sequences are amplitude modulated with different ones of the plurality of frequencies extracted from the sound signals; and delivering each of the plurality of stimulation pulse sequences to the recipient via one or more stimulation channels of the hearing prosthesis.

In another aspect, a method is provided. The method comprises: receiving sound signals at a hearing prosthesis; extracting at least one frequency from the sound signals; filtering the sound signals to generate channelized sound signals; determining a plurality of stimulation pulse sequences, wherein each of the plurality of stimulation pulse sequences corresponds to one of the channelized sound signals; determining a periodic probability for each of a plurality of the channelized sound signals, wherein a periodic probability indicates a degree of association between a channelized sound signal and the at least one frequency extracted from the sound signals; and amplitude modulating at least one of the plurality of stimulation pulse sequences based on a periodic probability associating a channelized sound signal corresponding to the at least one stimulation pulse sequence and the at least one frequency extracted from the sound signals.

In another aspect, a hearing prosthesis is provided. The hearing prosthesis comprises: one or more sound input elements configured to receive sound signals; a memory; a stimulator unit; and at least one processor configured to: estimate at least first and second different frequencies present within the received sound signals, determine at least first and second stimulation pulse sequences based on the sound signals, amplitude modulate the first stimulation pulse sequence based on the first frequency, and amplitude modulate the second stimulation pulse sequence based on the second frequency, wherein the stimulator unit is configured to deliver the first and second stimulation pulse sequences to a recipient of the hearing prosthesis.

BRIEF DESCRIPTION OF THE DRAWINGS

Embodiments of the present invention are described herein in conjunction with the accompanying drawings, in which:

FIG. 2 is a block diagram of a totally implantable cochlear implant, in accordance with certain embodiments presented herein;

FIG. 3 is a functional block diagram of a sound processing block, in accordance with certain embodiments presented herein;

FIG. 4 is a flowchart of a method in accordance with embodiments presented herein FIG. 5 is a functional block diagram illustrating channel modulation using a single sound source, in accordance with certain embodiments presented herein;

FIG. 6 is a functional block diagram illustrating channel modulation using multiple sound sources, in accordance with certain embodiments;

FIG. 14 is a flowchart of a method in accordance with embodiments presented herein; and FIG. 15 is flowchart of another method in accordance with embodiments presented herein.

DETAILED DESCRIPTION

Embodiments of the present invention are generally directed to techniques for enhancing a hearing/auditory prosthesis recipient's perception of multiple frequencies (e.g., multiple fundamental frequencies) present in received sound signals. The hearing prosthesis is configured to extract a plurality of frequencies from the received sound signals and to use the plurality of frequencies to modulate the amplitudes of different stimulation pulse sequences that are to be delivered to the recipient via different stimulation channels. The hearing prosthesis may also adapt a stimulation resolution of the stimulation pulse sequences when delivering the modulated stimulation pulses sequences to the recipient.

There are a number of different types of electrically-stimulating auditory/hearing prostheses in which embodiments of the present invention may be implemented. However, merely for ease of illustration, the techniques presented herein are primarily described with reference to one type of electrically-stimulating hearing prosthesis, namely a cochlear implant. However, it is to be appreciated that the techniques presented herein may be used in other electrically-stimulating auditory prostheses, such as auditory brainstem stimulators, electro-acoustic hearing prostheses, bimodal hearing prostheses, etc.

Figure 1A:
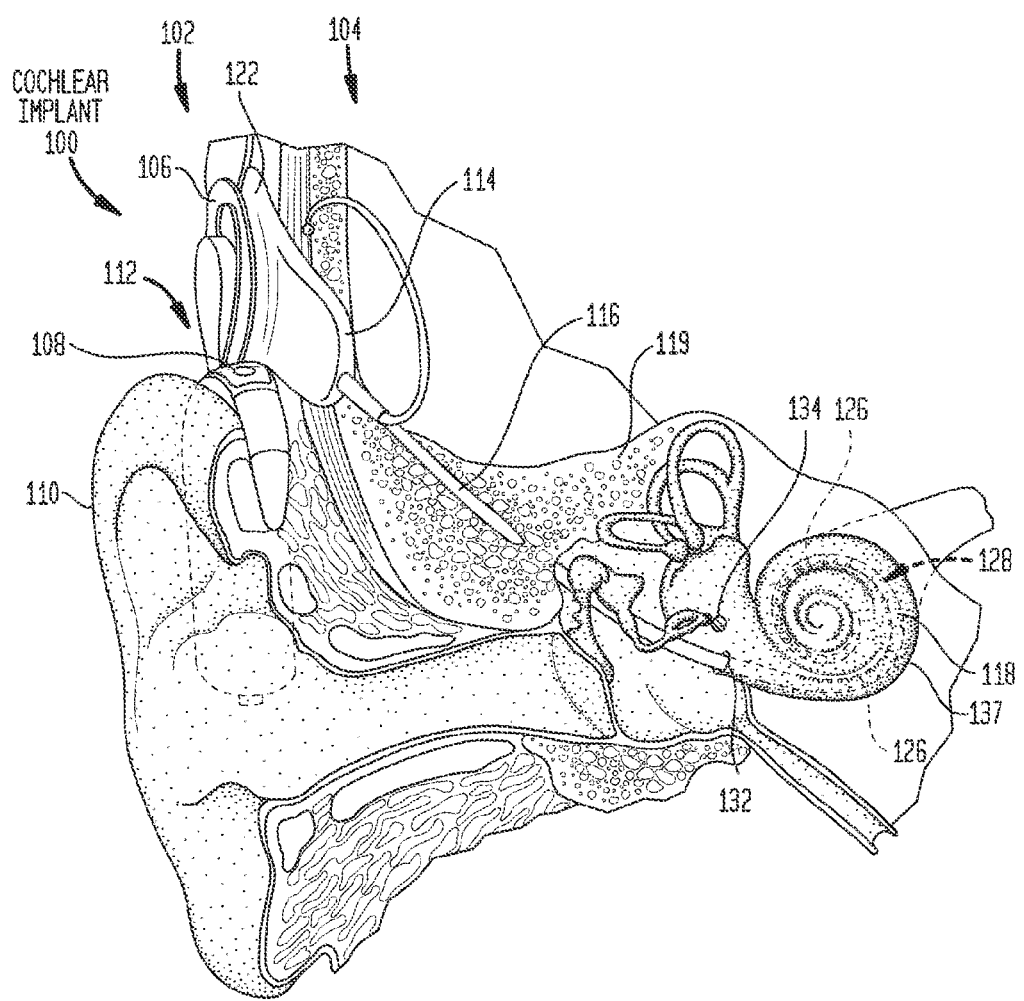
FIG. 1A is a schematic diagram illustrating a cochlear implant, in accordance with certain embodiments presented herein.
Figure 1B:
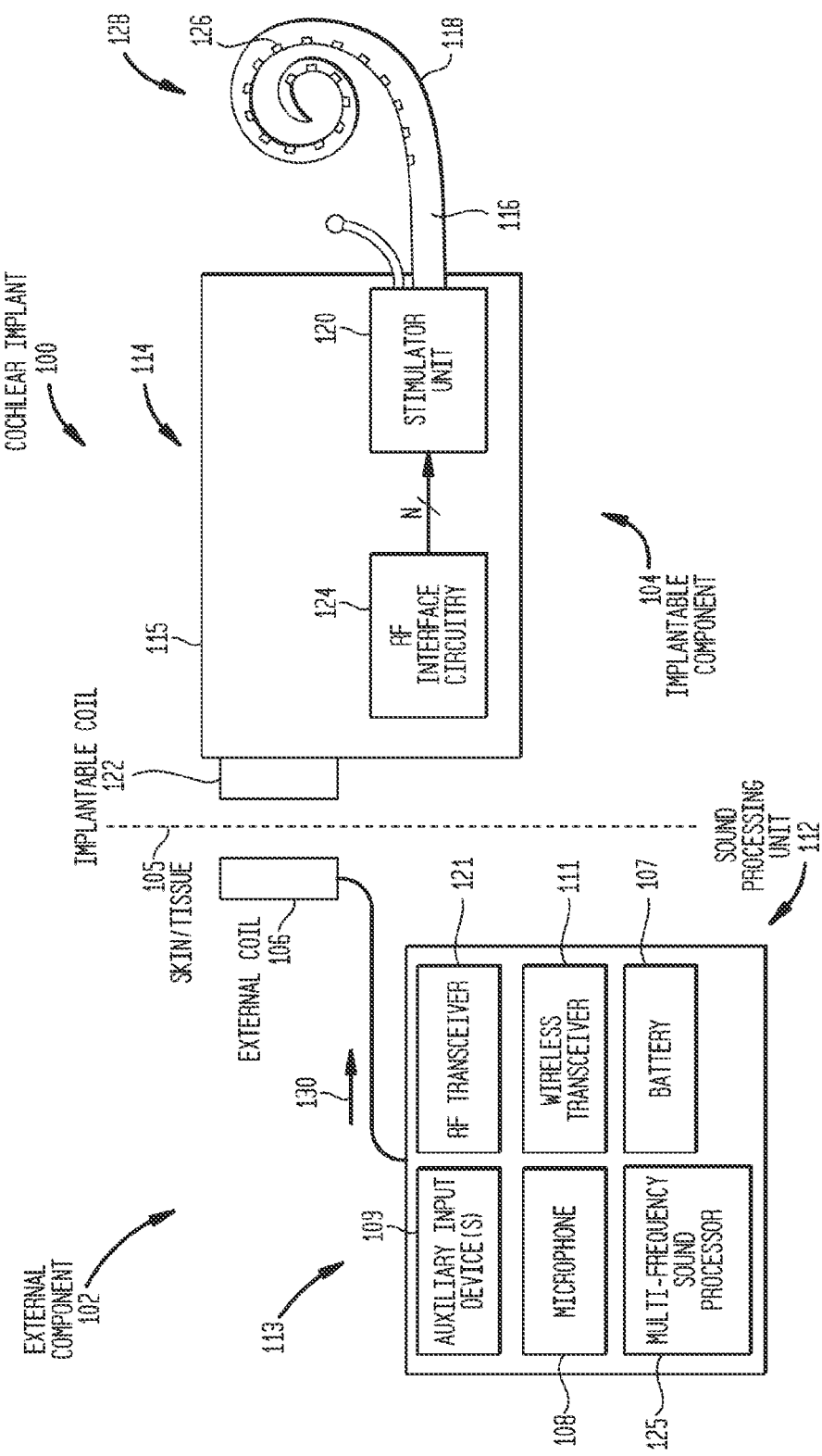
FIG. 1B is a block diagram of the cochlear implant of FIG. 1A.

FIG. 1A is a schematic diagram of an exemplary cochlear implant 100 configured to implement aspects of the techniques presented herein, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 113 for receiving input sound signals at a sound processing unit 112. In this example, the one or more input devices 113 include microphones 108 positioned by auricle 110 of the recipient configured to capture/receive input sound signals, one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112. Although not shown in FIG. 1A or 1B, the input devices 113 could also include, for example, telecoils or other types of inputs.

The sound processing unit 112 also includes, for example, at least one battery 107, a radio-frequency (RF) transceiver 121, and a multi-frequency sound processor 125. The multi-frequency sound processor 125 may be formed by one or more processors (e.g., one or more Digital Signal Processors (DSPs), one or more uC cores, etc.), memories, firmware, software, etc. arranged to perform operations described herein. That is, the multi-frequency sound processor 125 may be implemented as firmware elements, partially or fully implemented with digital logic gates in one or more application-specific integrated circuits (ASICs), by processors executing software (instructions) stored in memory, etc.

Returning to the specific example of FIGS. 1A and 1B, the implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. The implant body 114 also includes an internal/implantable coil 122 that is generally external to the housing 115, but which is connected to the RF interface circuitry 124 via a hermetic feedthrough (not shown in FIG. 1B).

As noted, stimulating assembly 118 is configured to be at least partially implanted in the recipient's cochlea 137. Stimulating assembly 118 includes a plurality of longitudinally spaced intra-cochlear electrical stimulating contacts (electrodes) 126 that collectively form a contact or electrode array 128 for delivery of electrical stimulation (current) to the recipient's cochlea. Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically couple the electrodes 126 to the stimulator unit 120.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the multi-frequency sound processor 125, which may be implemented in hardware, software, and/or a combination thereof. In general, the multi-frequency sound processor 125 is configured to convert input audio signals into stimulation control signals 130 for use in stimulating a first ear of a recipient (i.e., the processing block 125 is configured to perform sound processing on input audio signals received at the sound processing unit 112). Stated differently, the multi-frequency sound processor 125 (e.g., one or more processing elements implementing firmware, software, etc.) is configured to convert the captured input audio signals into stimulation control signals 130 that represent electrical stimulation for delivery to the recipient. The input audio signals that are processed and converted into stimulation control signals may be audio signals received via the sound input devices 108, signals received via the auxiliary input devices 109, and/or signals received via the wireless transceiver 111.

In accordance with certain embodiments presented herein, to generate the stimulation control signals 130, the multi-frequency sound processor 125 is configured to identify and track multiple sound sources (track sound components associated with received sound signals), as well as to extract at least one frequency (e.g., the fundamental frequency) of each of the sound sources. The multi-frequency sound processor 125 is also configured to generate the stimulation control signals 130 such that the multiple frequencies extracted from the sound signals are encoded in the final stimulation pulse sequences that are delivered to the recipient. The multi-frequency sound processor 125 may also enable the different frequencies to be individually controlled.

In the embodiment of FIG. 1B, the stimulation control signals 130 are provided to the RF transceiver 121, which transcutaneously transfers the stimulation control signals 130 (e.g., in an encoded manner) to the implantable component 104 via external coil 106 and implantable coil 122. That is, the stimulation control signals 130 are received at the RF interface circuitry 124 via implantable coil 122 and provided to the stimulator unit 120. The stimulator unit 120 is configured to utilize the stimulation control signals 130 to generate electrical stimulation signals (e.g., sequences of stimulation (current) pulses) for delivery to the recipient's cochlea via one or more stimulation channels each formed by one or more stimulating contacts 126. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

FIGS. 1A and 1B illustrate an arrangement in which the cochlear implant 100 includes an external component. However, it is to be appreciated that embodiments of the present invention may be implemented in cochlear implants or auditory prostheses having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge an internal power source (battery) 207. External device 202 may be, for example, a dedicated charger or a conventional cochlear implant sound processor.

Cochlear implant 200 includes an implant body (main implantable component) 214, one or more input elements 213 for capturing/receiving input audio signals (e.g., one or more implantable microphones 208 and a wireless transceiver 211), an implantable coil 222, and an elongate intra-cochlear stimulating assembly 118 as described above with reference to FIGS. 1A and 1B. The microphone 208 and/or the implantable coil 222 may be positioned in, or electrically connected to, the implant body 214. The implant body 214 further comprises the battery 207, RF interface circuitry 224, a multi-frequency sound processor 225, and a stimulator unit 220 (which is similar to stimulator unit 120 of FIGS. 1A and 1B). The multi-frequency sound processor 225 may be similar to multi-frequency sound processor 125 of FIGS. 1A and 1B.

In the embodiment of FIG. 2, the one or more implantable microphones 208 are configured to receive input audio signals. The multi-frequency sound processor 225 is configured to convert received signals into stimulation control signals 230 for use in stimulating a first ear of a recipient. Stated differently, the multi-frequency sound processor 225 is configured to convert the input audio signals into stimulation control signals 230 that represent electrical stimulation for delivery to the recipient. Similar to the multi-frequency sound processor 125 of FIGS. 1A and 1B, to generate the stimulation control signals 230, the multi-frequency sound processor 225 is configured to identify and track multiple sound sources (sound components associated with sound sources), as well as to extract at least one frequency (e.g., the fundamental frequency) associated with each of the sound sources. The multi-frequency sound processor 225 is also configured to generate the stimulation control signals 230 such that the multiple frequencies are encoded in the final stimulation pulse sequences that are delivered to the recipient. The multi-frequency sound processor 225 may also enable the different frequencies to be individually controlled.

As noted above, FIGS. 1A and 1B illustrate an embodiment in which the external component 102 includes the multi-frequency sound processor 125. As such, in the illustrative arrangement of FIGS. 1A and 1B, the stimulation control signals 130 are provided to the implanted stimulator unit 120 via the RF link between the external coil 106 and the internal coil 122. However, in the embodiment of FIG. 2 the multi-frequency sound processor 225 is implanted in the recipient. As such, in the embodiment of FIG. 2, the stimulation control signals 230 do not traverse the RF link, but instead are provided directly to the stimulator unit 220. The stimulator unit 220 is configured to utilize the stimulation control signals 230 to generate electrical stimulation signals (e.g., sequences of stimulation (current) pulses) that are delivered to the recipient's cochlea via one or more stimulation channels.

A recipient's cochlea is tonotopically mapped, that is, partitioned into regions each responsive to sound signals in a particular frequency range. In general, the basal region of the cochlea is responsive to higher frequency sounds, while the more apical regions of the cochlea are responsive to lower frequency sounds. The tonopotic nature of the cochlea is leveraged in cochlear implants such that specific acoustic frequencies are allocated to the electrode(s) of the stimulating assembly that are positioned close to the corresponding tonotopic region of the cochlea (i.e., the region of the cochlea that would naturally be stimulated in acoustic hearing by the acoustic frequency). That is, in a cochlear implant, specific frequency bands are each mapped to a set of one or more electrodes that are used to stimulate a selected (target) population of cochlea nerve cells. The frequency bands, and associated electrode(s), form a "stimulation channel" that delivers stimulation signals to the recipient. During operation, a cochlear implant sound processor encodes or maps different frequency portions of the received sound signals sound signals to the electrodes that should be used to deliver stimulation signals representing the different frequency portions.

Certain conventional sound encoding (coding) strategies for electrically-stimulating auditory prostheses are effective in enabling a recipient to correctly perceive the fundamental frequency (F0) associated with a single source of sound (sound source). However, many real-world environments include multiple sound sources with different fundamental frequencies, or may comprise a single sound source that includes multiple harmonics or concurrent pitches. Conventional sound coding strategies generally lack the ability to appropriately capture and deliver multiple fundamental frequencies (F0s) from these different sound sources and/or multiple harmonics included in a single sound source. Consequently, recipients may not have access to the auditory cues necessary for accurate perception of multiple frequencies in received sound signals, such as, musical harmonies, musical compositions with multiple instruments, speech signals from multiple talkers, or in other situations with multiple sound sources, multiple harmonics, and/or concurrent pitches.

Accordingly, presented herein are techniques that improve a recipient's perception of multiple frequencies (e.g., multiple F0s, multiple harmonics, etc.) included within sound signals received at a hearing prosthesis (i.e., multiple frequencies simultaneously received at the prosthesis). As described further below, the techniques presented herein identify and track sound components associated with different sound sources that are included within received sound signals, extract frequencies of each sound source, encode the multiple frequencies within stimulation signals delivered to the recipient, and allow the different frequencies to be individually controlled. As noted, these techniques may be implemented by a multi-frequency sound processor, such as multi-frequency sound processors 125 and 225, of an electrically-stimulating hearing prosthesis.

FIG. 3 is a functional block diagram illustrating an example multi-frequency sound processor configured to implement the techniques presented herein. For ease of description, the multi-frequency sound processor of FIG. 3 is referred to as multi-frequency sound processor 325.

In the embodiment of FIG. 3, the multi-frequency sound processor 325 comprises: a filterbank module 334, an envelope extraction module 336, a channel selection module 338, and a stimulation pulse determination module 340. Modules 334, 336, 338, and 340 are sometimes collectively referred to herein as a "sound processing path" 358 for the multi-frequency sound processor 325. However, in addition to the sound processing path 358 (i.e., modules 336, 338, and 340), the multi-frequency sound processor 325 also comprises a fundamental frequency module 342, an environmental classification module 344, a periodic probability estimator module 346, a channel modulation module 348, a channel focusing control module 350, an automatic control module 352, and a user control module 354.

It is to be appreciated that the functional modules shown in FIG. 3 generally represent functions/operations that can be performed in accordance with embodiments presented herein, and do not necessarily imply any specific structure for the multi-frequency sound processor 325. For example, the modules shown in FIG. 3 may be implemented as firmware elements, partially or fully implemented with digital logic gates in one or more application-specific integrated circuits (ASICs), by processors executing software (instructions) stored in memory, etc. As described further below, it is also to be appreciated that the specific combination of functional modules shown in FIG. 3 are illustrative and that multi-frequency sound processors in accordance with certain embodiments may include only a subset of the modules shown in FIG. 3 and/or other functional modules that, for ease of illustration, have been omitted from FIG. 3.

In the example of FIG. 3, sound signals are received/captured by one or more input devices (e.g., microphones, audio input port, etc.) and provided as input sound signals 331 to a filterbank module (filterbank) 334. The input sound signals 331 may also be provided to the fundamental frequency module 342 and the environmental classification module 344. Although not shown in FIG. 3, in certain embodiments a pre-filterbank processing module may be present and configured to, as needed, combine signals from different sound input elements to generate the input sound signals 331 and to, again as needed, prepare those signals for subsequent processing by the filterbank module 334, etc.

In operation, the filterbank module 334 generates a suitable set of bandwidth limited channels, or frequency bins, that each includes a spectral component of the received sound signals. That is, the filterbank module 334 may comprise a plurality of band-pass filters that separate the input sound signals 331 into multiple bands/channels, each one carrying a single frequency sub-band of the original signal (i.e., frequency components of the received sounds signal).

The channels created by the filterbank module 334 are sometimes referred to herein as sound processing channels, and the sound signal components within each of the sound processing channels are sometimes referred to herein as band-pass filtered signals or channelized signals. The band-pass filtered or channelized signals created by the filterbank module 334 are processed (e.g., modified/adjusted) as they pass through the sound processing path 358. As such, the band-pass filtered or channelized signals are referred to differently at different stages of the sound processing path 358. However, it will be appreciated that reference herein to a band-pass filtered signal or a channelized signal may refer to the spectral component of the received sound signals at any point within the sound processing path 358 (e.g., pre-processed, processed, selected, etc.).

At the output of the filterbank module 334, the channelized signals are initially referred to herein as pre-processed signals 335. The number 'm' of channels and pre-processed signals 335 generated by the filterbank module 334 may depend on a number of different factors including, but not limited to, implant design, number of active electrodes, coding strategy, and/or recipient preference(s). In certain arrangements, twenty-two (22) channelized signals are created and the sound processing path 358 is said to include 22 channels.

The pre-processed signals 335 are provided to the envelope extraction module 336, which determines/extracts the amplitude envelopes 337 of the processed signals 335 within each of the channels. These envelopes 337 are provided to the channel selection module 338, as well as to the channel modulation module 348. The channel selection module 338 is configured to perform a channel selection process to select, according to one or more selection rules, which of the 'm' channels should be use in hearing compensation. The signals selected at channel selection module 338 are represented in FIG. 3 by arrow 339 and are referred to herein as selected channelized signals or, more simply, selected signals.

In the embodiment of FIG. 3, the channel selection module 338 selects a subset 'n' of the 'm' envelopes 337 for use in generation of electrical stimulation for delivery to a recipient (i.e., the sound processing channels are reduced from 'm' channels to 'n' channels). In one specific example, the 'n' largest amplitude channels (maxima) from the 'm' available combined channel signals/masker signals is made, with 'm' and 'n' being programmable during initial fitting, and/or operation of the prosthesis. It is to be appreciated that different channel selection methods could be used, and are not limited to maxima selection.

It is also to be appreciated that, in certain embodiments, the channel selection module 338 may be omitted. For example, certain arrangements may use a continuous interleaved sampling (CIS), CIS-based, or another non-channel selection sound coding strategy.

The stimulation pulse determination module 340 is configured to map the amplitudes of the selected signals 339 (or the envelopes 337 in embodiments that do not include channel selection) into a set of output signals 330 (e.g., stimulation commands) that represent the attributes of the electrical stimulation signals that are to be delivered to the recipient so as to evoke perception of at least a portion of the received sound signals. This channel mapping may include, for example, threshold and comfort level mapping, dynamic range adjustments (e.g., compression), volume adjustments, etc., and may encompass selection of various sequential and/or simultaneous stimulation strategies. Further details regarding the operation of the stimulation pulse determination module 340 are provided below.

Although not shown in FIG. 3, the sound processing path 358 may include a processing module that is configured to perform a number of sound processing operations on the channelized signals. These sound processing operations include, for example, channelized gain adjustments for hearing loss compensation (e.g., gain adjustments to one or more discrete frequency ranges of the sound signals), noise reduction operations, speech enhancement operations, etc., in one or more of the channels. In certain implementations, these operations may be performed in the stimulation pulse determination module 340.

As noted above, in addition to modules 336, 338, and 340, the multi-frequency sound processor 325 also comprises the fundamental frequency module 342, the environmental classification module 344, the periodic probability estimator module 346, the channel modulation module 348, the channel focusing control module 350, the automatic control module 352, and the user control module 354. Each of these modules 342, 344, 346, 348, 350, 352, and 354, may perform supplemental operations that, in accordance with the techniques presented herein, control or affect the operations performed in the sound processing path 358 to generate the stimulation control signals 330. For ease of description, the operation of modules 342, 344, 346, 348, 350, 352, and 354, are described further below with reference to FIGS. 4-12.

More specifically, FIG. 4 is a high-level flowchart of a method 460 in accordance with embodiments presented herein. Method 460 begins 461 where the environmental classification module 344 evaluates/analyzes the input sound signals and determines the sound class/category/environment of the sound signals. That is, the environmental classification module 344 is configured to use the received sound signals to "classify" the ambient sound environment and/or the sound signals into one or more sound categories (i.e., determine the input signal type). The sound class or environment may include, but are not limited to, "Speech," "Noise," "Speech+Noise," "Wind," "Music," and "Quiet." The environmental classification module 344 may also estimate the signal-to-noise ratio (SNR) of the sound signals. In one example, the operations of the environmental classification module 344 are performed using the input sound signals 331. The environmental classification module 344 generates sound classification information/data 341. The sound classification data 341 represents the sound class of the sound signals and, in certain examples, the SNR of the sound signals.

In certain examples, the environmental classification module 344 operates a gating function for the techniques presented herein. That is, certain sound classes may benefit from pitch and spectral resolution enhancements (e.g., Music, Speech, speech-in-noise), while others (e.g., Wind, Noise, Quiet) may not. If the environmental classification module 344 determines that the sound class of the input sound signals matches a sound class that can benefit from pitch and spectral resolution enhancements, then the sound classification data 341 can be provided to the fundamental frequency module 342 to trigger subsequent operations. Stated differently, in certain examples, the operations described below with reference to 462-467 may be performed only when the sound signals correspond to certain sound classes, while other sound signals will be processed according to standard techniques (e.g., advanced combination encoders (ACE)/continuous interleaved sampling-like strategies with monopolar stimulation).

Returning to FIG. 4, at 462 the fundamental frequency module 342 estimates one or more (e.g., multiple) fundamental frequencies (F0s) of the input sound signals. That is, the fundamental frequency module 342 is configured to analyze the input sound signals and extract one or more fundamental frequencies present therein. A number of different techniques that are based on temporal methods, spectral methods, statistical methods or data-driven approaches can be used for this purpose.

At 463, the fundamental frequency module 342 is configured to track the sound sources across time (i.e., track, over time, sound components associated with each of the plurality of sound sources) based on their associated F0 so that a specific sound source (i.e., sound components associated with a particular sound source) can be delivered to the same channel (set of electrodes) or the same ear, a specific sound source to be tracked over time, including variations in F0 attributed to the same sound source. For example, methods based on temporal continuity criteria or amplitude modulation cues could be used to track multiple sources/F0s across time.

As used herein, reference to a sound source as being "included in," or otherwise as being part of, the received sound signals is to be construed as reference to received sound components of the sound signals that are generated by the sound source. For example, reference to sound signals that include multiple sound sources refers to sound signals that include sound components each generated by one of the multiple sound sources.

For example, in certain embodiments, spectral filtering of harmonics may be used to identify and track the fundamental frequencies (F0s) of the input sound signals. In such examples, the fundamental frequency module 342 detects all salient spectral peaks while the spectrum typically contains some low-level broadband energy due to noise and spectral leakage. The fundamental frequency module 342 estimates pitch trajectories over all time frames using a multi-pitch estimator and matches spectral peaks to harmonics. Fitters are constructed to separate the spectral peaks or "harmonics" associated with one of the extracted pitches from the mixed spectrum In other embodiments, temporal autocorrelation functions may be used to identify and track the fundamental frequencies (F0s) of the input sound signals. In such examples, the fundamental frequency module 342 divides the input sound signals into two channels or ranges (e.g., below and above 1000 Hertz (Hz)). The fundamental frequency module 342 computes a "generalized" autocorrelation of the low-channel signal and of the envelope of the high-channel signal, and sums the autocorrelation functions. The summary autocorrelation function (SACF) is further processed to obtain an enhanced SACF (ESACF). The SACF and ESACF representations are used in observing the periodicities of the input signal.

In other embodiments, harmonicity and spectral smoothness may be used to identify and track the fundamental frequencies (F0s) of the input sound signals. In such examples, the fundamental frequency module 342 operates iteratively by estimating and removing the most prominent F0 from the mixture signal. The term predominant-F0 estimation refers to a crucial stage where the F0 of the most prominent sound is estimated in the presence of other harmonic and noisy sounds. To achieve this, the harmonic frequency relationships of simultaneous spectral components are used to group them to sound sources. An algorithm is proposed which is able to handle inharmonic sounds. These are sounds for which the frequencies of the overtone partials (harmonics) are not in exact integer ratios. In a subsequent stage, the spectrum of the detected sound is estimated and subtracted from the mixture. This stage utilizes the spectral smoothness principle, which refers to the expectation that the spectral envelopes of real sounds tend to be slowly varying as a function of frequency. In other words, the amplitude of a harmonic partial is usually close to the amplitudes of the nearby partials of the same sound. The estimation and subtraction steps are then repeated for the residual signal.

It is to be appreciated that the above techniques for identifying and tracking the fundamental frequencies (F0s) of the input sound signals are merely illustrative and that embodiments presented herein may alternatively make use of a number of other techniques. Regardless of the technique used, the fundamental frequency module 342 provides the identified and tracked sound sources, represented in FIG. 3 by arrow 343, to the periodic probability estimator 346.

Returning to FIG. 4, at 464 the periodic probability estimator 346 is configured to estimate the periodic probability of the channels present in the pre-processed signals 335 generated by the filterbank module 334. That is, the periodic probability estimator 346 is used to estimate the probability that the signal (e.g., harmonics) present in any given frequency channel is related to an estimated F0 frequency (i.e., contains frequency components, or partials, that are an integer multiple of the estimated F0 frequency, and/or contains periodicity in its envelope that is equal to the estimated F0 frequency). This functionality could be extended so that harmonics in each channel are compared against all the available F0s in the signal to obtain the periodic probabilities for all F0s. These probability estimates can be further used to separate out sources corresponding to the individual F0s that were identified by the fundamental frequency module 342.

In certain embodiments, the periodic probability estimator 346 employs two methods, one for low-frequency channels (e.g., 0-2 kHz) and a different one for high-frequency channels (e.g., 2 kHz). For low-frequency channels, the periodic probability estimator 346 calculates the ratio of the power in the harmonic frequency bins to the total power within that channel A Gaussian sieve process is used to filter the harmonic regions of the bandwidth within each channel Next, the above ratios are scaled by the total power of the low-frequency channels (0-2 kHz) to obtain the probability of the channel containing the harmonic of an estimated F0. For high-frequency channels, the channel periodic probability may be estimated by determining whether the period of the channel envelope signal is equal to (or close to) the period of the estimated F0 frequency. This is achieved by high-pass filtering the wide-bandwidth channel envelope signal obtained from the filterbank module, and maintaining a history of it in a buffer (e.g., of approximately 28 ms duration).

It is to be appreciated that the above techniques for estimating the periodic probability for a given channel are merely illustrative and that embodiments presented herein may alternatively make use of a number of other techniques. Regardless of the technique used, the periodic probability estimator module 346 provides the periodic probability (or probabilities) determined for each channel to the channel modulation module 348. In FIG. 3, the determined periodic probability (or probabilities), which are represented by arrow 345, are provided to the channel modulation module 348.

In the case of multiple F0s, the fundamental frequency module 342f will output one or more F0s. In such examples, the periodic probability estimator 346 can implement the above processes repeatedly for each estimated F0. That is, for an M-channel cochlear implant, there will be M periodic probabilities per estimated F0. For example, for 2 different F0s, there will be m periodic probabilities for the first F0 and a second set of M periodic probabilities for the second F0. In other words, each channel will have two probabilities (or K probabilities) corresponding to the two sources (or K sources).

Returning to FIG. 4, at 465 the channel modulation module 348 is configured to adapt channel amplitude modulations applied in the sound processing path according to the periodic probability determined for the given channel More specifically, as noted, the envelope extraction module 336 determines the channel envelope signals 337 (envelopes) from the bandpass filtered signals 335, and slowly-varying channel envelope signals are further extracted from the original set of channel envelopes. The slowly-varying channel envelope signals are amplitude modulated by a given frequency, determined by the fundamental frequency module 342. In certain examples, the modulated channel envelopes, represented in FIG. 3 by arrow 347, are mixed with the non-modulated channel envelopes at a mixing ratio determined by the associated periodic probability. An example of such a process is shown in FIG. 5 (i.e., a Sound Source "A" is identified and the associated estimated periodic probability, for a given channel, is used to control the mixing ratio for that channel).

The sequences of stimulation pulses in each of the individual channels can be amplitude modulated according to a number of different ways and, in certain embodiments, the amplitude modulations may be based on multiple identified frequencies (e.g., multiple F0s, multiple harmonics, etc.). For example, the sequences of stimulation pulses in each channel may be amplitude modulated with different F0s corresponding to separate sound sources or with different frequencies that are harmonics of the F0 of a single sound source. The dominant sound source in a given frequency channel, as determined by the amplitude of the sound source, may be used to select the F0 for use in modulating the pulses in that channel. Alternatively, channels may be grouped and allocated to different sound sources. For example, FIG. 6 illustrates an example of such a process in which the periodic probabilities associated with multiple sources are used to control a mixing ratio for mixing modulated channel envelopes with non-modulated channel envelopes (i.e., Sound Sources "A," "B," "C," and "D" are identified and the estimated periodic probabilities, for a given channel, associated with one or more of these sound sources is used to control the mixing ratio for that channel).

In one embodiment in which multiple F0s are identified, the sequences of stimulation pulses in each channel can be amplitude modulated in accordance with (based on) the source F0 that results in maximum periodic probability among all the source F0s for that channel (i.e., channel modulation based on strength of harmonicity). In other embodiments in which multiple F0s are identified, the sequences of stimulation pulses in each channel can be modulated based on the F0 for the source that is selected by the user (e.g., via user input module 354 in FIG. 3) or through an automatic control (e.g., via automatic control module 352), sometimes referred to as channel modulation based on source selection. In further embodiments in which multiple F0s are identified, the sequences of stimulation pulses in all of the channels may be modulated based on the source that results in a greater number of higher periodic probabilities across all the channels. For example, if twelve (12) out of twenty (20) channels result in higher periodic probabilities for source B compared to that of source A, then the sequences of stimulation pulses in all 20 channels may be amplitude modulated according to the periodic probabilities and F0 corresponding to source B. In another embodiment, all channels can be modulated according to the periodic probabilities of the source that corresponds to the largest periodic probability on any channel (i.e., channel modulations based on dominant source/channel).

Returning again to FIG. 4, at 466 the channel focusing control module 350 is configured to adapt a stimulus resolution of the sequence of modulated stimulation pulses, when delivered via a stimulation channel That is, certain embodiments presented herein combine the use of periodic probability estimation and F0 channel modulation with stimulus resolution adaptions, such as stimulation focusing, to provide additional frequency perception (pitch) enhancements. For example, it may be desirable to deliver focused stimulation for periodic signals such as vowels and melodic musical instruments to improve the perception of simultaneously received formants and harmonics. However, non-periodic signals, such as unvoiced consonants and percussive musical instruments, may not benefit as much from focused stimulation. Therefore, the degree of stimulus resolution adaption (e.g., focusing) is reduced for non-periodic sounds, resulting in more monopolar-like stimulation and potential power savings. In certain embodiments, the stimulus resolution adaption is implemented by adjusting the defocusing index, which ranges between 0 (i.e., fully focused stimulation) and 1 (i.e., monopolar stimulation).

Improved channel independence via focused stimulation may also provide better representation of F0 modulations, particularly when different F0s are represented across different channels. Therefore, adaptive focusing may be further combined with the channel modulations described above to explicitly represent F0s and/or harmonics estimated from the sound signals. Channels with high periodic probability will be stimulated with a lower defocusing index and a higher mixing ratio of the modulated channel envelope, while channels with low periodic probability will receive a higher defocusing index and a lower mixing ratio.

In one example, the channel focusing control module 350 may adjust operations of the stimulation pulse determination module 340 to set the stimulus resolution of the delivered electrical stimulation signals (pulse sequences) based on an associated periodic probability. In one embodiment, the spatial/spectral attributes of the stimulus resolution are set by switching between different channel/electrode configurations, such as between monopolar stimulation, wide/defocused stimulation, focused (e.g., multipolar current focusing) stimulation, etc. In operation, the channel focusing control module 350 may provide focusing control inputs, represented in FIG. 3 by arrow 351, to the stimulation pulse determination module 340 to set the stimulus resolution of the delivered electrical stimulation signals based on the periodic probability.

FIGS. 7A-7E are a series of schematic diagrams illustrating exemplary electrode currents and stimulation patterns for five (5) different stimulus resolutions (i.e., different defocusing indices). It is to be appreciated that the stimulation patterns shown in FIGS. 7A-7E are generally illustrative and that, in practice, the stimulation current may spread differently in different recipients.

Figure 7A:
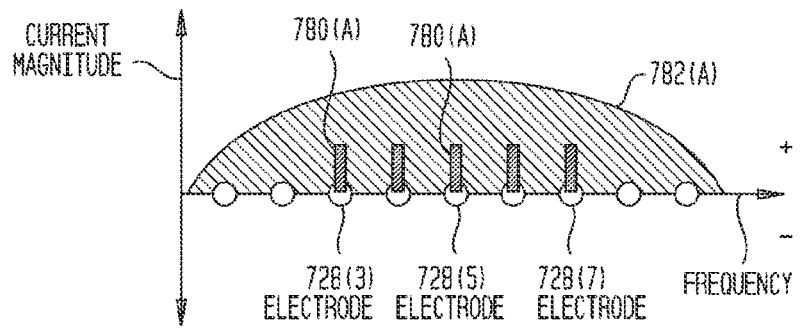
FIGS. 7A, 7B, 7C, 7D, and 7E are schematic diagrams illustrating the adaption of spatial resolution of electrical stimulation signals based on periodic probabilities, in accordance with certain embodiments presented herein.
Figure 7B:
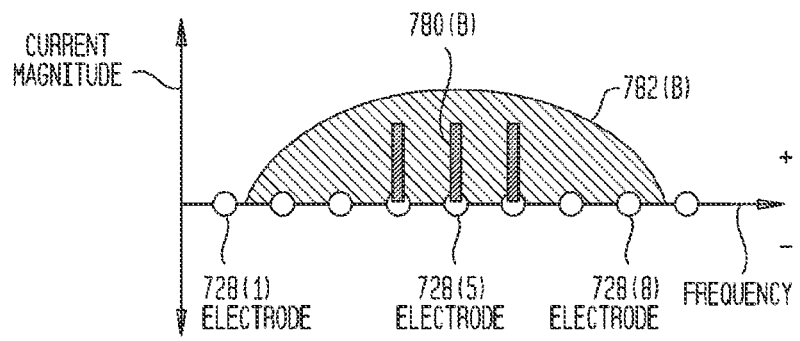
Figure 7C:
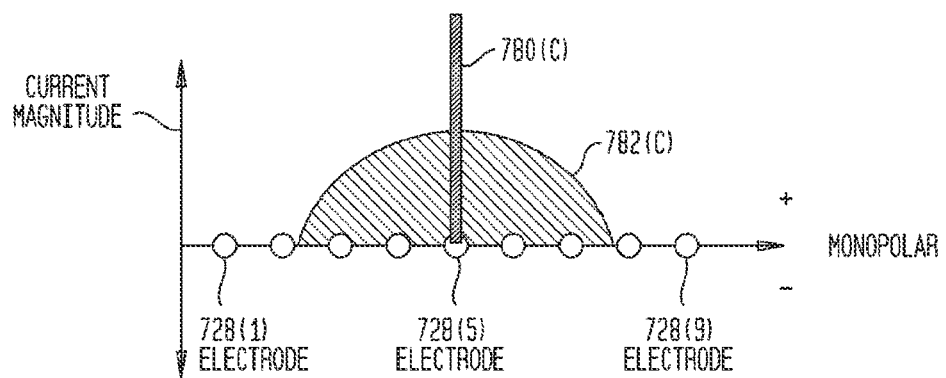

Each of the FIGS. 7A-7E illustrates a plurality of electrodes shown as electrodes 728(1)-728(9), which are spaced along the recipient's cochlea frequency axis (i.e., along the basilar membrane). FIGS. 7A-7E also include solid lines of varying lengths that extend from various electrodes to generally illustrate the intra-cochlear stimulation current 780(A)-780(E) delivered in accordance with a particular channel configuration. However, it is to be appreciated that stimulation is delivered to a recipient using charge-balanced waveforms, such as biphasic current pulses and that the length of the solid lines extending from the electrodes in each of FIGS. 7A-7E illustrates the relative "weights" that are applied to both phases of the charge-balanced waveform at the corresponding electrode in accordance with different channel configurations. As described further below, the different stimulation currents 780(A)-780(E) (i.e., different channel weightings) results in different stimulation patterns 782(A)-782(E), respectively, of voltage and neural excitation along the frequency axis of the cochlea Referring first to FIG. 7C, shown is the use of a monopolar channel configuration where all of the intra-cochlear stimulation current 780(C) is delivered with the same polarity via a single electrode 728(5). In this embodiment, the stimulation current 780(C) is sunk by an extra-cochlear return contact which, for ease of illustration, has been omitted from FIG. 7C. The intra-cochlear stimulation current 780(C) generates a stimulation pattern 782(C) which, as shown, spreads across neighboring electrodes 728(3), 728(4), 728(6), and 728(7). The stimulation pattern 782(C) represents the spatial attributes (spatial resolution) of the monopolar channel configuration.

FIGS. 7A and 7B illustrate wide or defocused channel configurations where the stimulation current is split amongst an increasing number of intracochlear electrodes and, accordingly, the width of the stimulation patterns increases and thus provide increasingly lower spatial resolutions. In these embodiments, the stimulation current 780(A) and 780(B) is again sunk by an extra-cochlear return contact which, for ease of illustration, has been omitted from FIGS. 7A and 7B.

More specifically, in FIG. 7B the stimulation current 780(B) is delivered via three electrodes, namely electrodes 728(4), 728(5), and 728(6). The intra-cochlear stimulation current 780(B) generates a stimulation pattern 782(B) which, as shown, spreads across electrodes 728(2)-728(8). In FIG. 7A, the stimulation current 780(A) is delivered via five electrodes, namely electrodes 728(3)-728(7). The intra-cochlear stimulation current 780(A) generates a stimulation pattern 782(A) which, as shown, spreads across electrodes 728(1)-728(9). In general, the wider the stimulation pattern, the lower the spatial resolution of the stimulation signals.

Figure 7D:
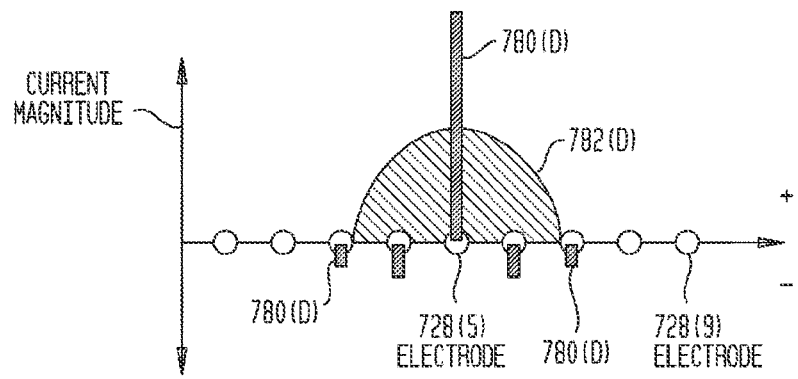
Figure 7E:
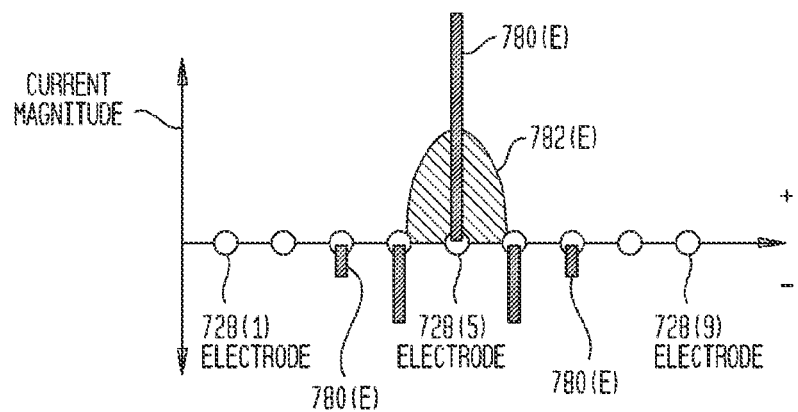

FIGS. 7D and 7E illustrate focused channel configurations where intracochlear compensation currents are added to decrease the spread of current along the frequency axis of the cochlea. The compensation currents are delivered with a polarity that is opposite to that of a primary/main current. In general the more compensation current at nearby electrodes, the more focused the resulting stimulation pattern (i.e., the lower the width of the stimulus patterns increase and thus increasingly higher spatial resolutions). That is, the spatial resolution is increased by introducing increasing large compensation currents on electrodes surrounding the central electrode with the positive current.

More specifically, in FIG. 7D positive stimulation current 780(D) is delivered via electrode 728(5) and stimulation current 780(D) of opposite polarity is delivered via the neighboring electrodes, namely electrodes 728(3), 728(4), 728(6), and 728(7). The intra-cochlear stimulation current 780(D) generates a stimulation pattern 782(D) which, as shown, only spreads across electrodes 728(4)-728(6). In FIG. 7E, positive stimulation current 780(E) is delivered via electrode 728(5), while stimulation current 780(E) of opposite polarity is delivered via the neighboring electrodes, namely electrodes 728(3), 728(4), 728(6), and 728(7). The intra-cochlear stimulation current 780(E) generates a stimulation pattern 782(E) which, as shown, is generally localized to the spatial area adjacent electrode 728(5).

The difference in the stimulation patterns 782(D) and 782(E) in FIGS. 7D and 7E, respectively, is due to the magnitudes (i.e., weighting) of opposite polarity current delivered via the neighboring electrodes 728(3), 728(4), 728(6), and 728(7). In particular, FIG. 7D illustrates a partially focused configuration where the compensation currents do not fully cancel out the main current on the central electrode and the remaining current goes to a far-field extracochlear electrode (not shown). FIG. 7E is a fully focused configuration where the compensation currents fully cancel out the main current on the central electrode 728(5) (i.e., no far-field extracochlear electrode is needed).

As noted, FIGS. 7A-7E collectively illustrate techniques for adjusting the spatial resolution (i.e., adjusting the spatial attributes of the electrical stimulation) based on estimated periodic probabilities, in accordance with embodiments presented herein. However, also as noted, it is to be appreciated that other methods for altering the stimulus resolution could be used in combination with, or as an alternative to, adjustments to the spatial resolution enabled by different stimulation strategies. For example, another technique for adapting the stimulus resolution includes varying the temporal resolution via pulse rate (i.e., higher pulse rates for higher temporal resolutions and lower pulse rates for lower temporal resolutions) based on estimated periodic probabilities.

Another technique for adapting the stimulus resolution based on estimated periodic probabilities includes varying the number of stimulation sites of the stimulation by changing the number of maxima in the channel selection. For example, the number of stimulation sites can be increased by increasing the number of channels selected by the channel selection module 338 and decreased by decreasing the number of channels selected by the channel selection module 338.

A still other technique for adapting the stimulus resolution based on estimated periodic probabilities includes varying the frequency resolution. The frequency resolution of the filterbank module 334 can be increased by, for example, in an FFT filterbank using a higher-point FFT. The frequency resolution of the filterbank module 334 can be decreased by, for example in an FFT filterbank using a lower-point FFT.

Again, returning to FIG. 4, at 467, in certain embodiments presented herein, user-based or automatic control inputs may be used to control the identified sound sources, channel modulations, or focusing (e.g., control one or more of the fundamental frequency module 342, channel modulation module 348, or the channel focusing control module 350). For example, the individual sound sources that are identified and tracked by the fundamental frequency module 342 may be controlled in a number of ways. Bilateral controls include the option to purposefully deliver different pitches or sound sources to the same or different ears. This is done either manually by the user or may be automated based on, for example, estimated spatial location in a real-world situation, a recorded stereo sound file, etc. Users may select sound sources preferentially to either enhance the pitch or loudness of a given source or to de-emphasize or mute the source. Sound source selection may also be automated using, for example, head position, gaze direction, or EEG responses to predict the desired source of the user.

Figure 8:
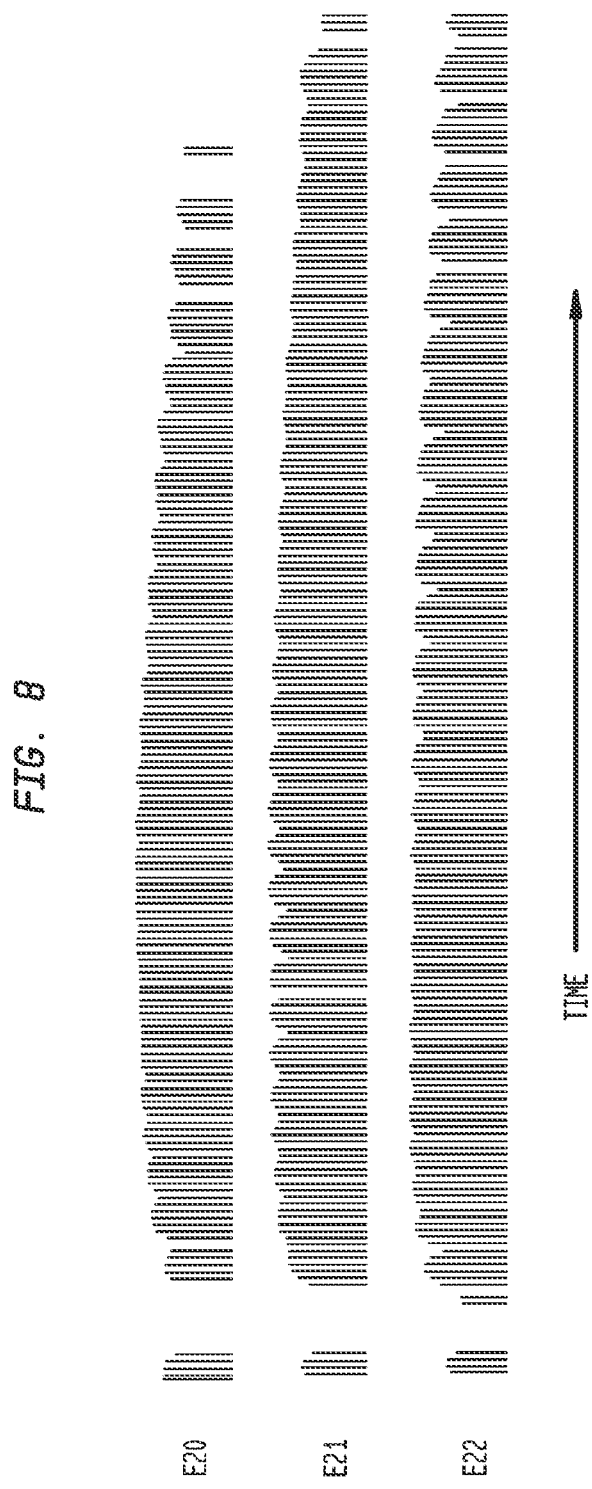
FIG. 8 is an electrodogram illustrating three sequences of fixed rate stimulation pulses modulated based on channel envelopes.
Figure 9:
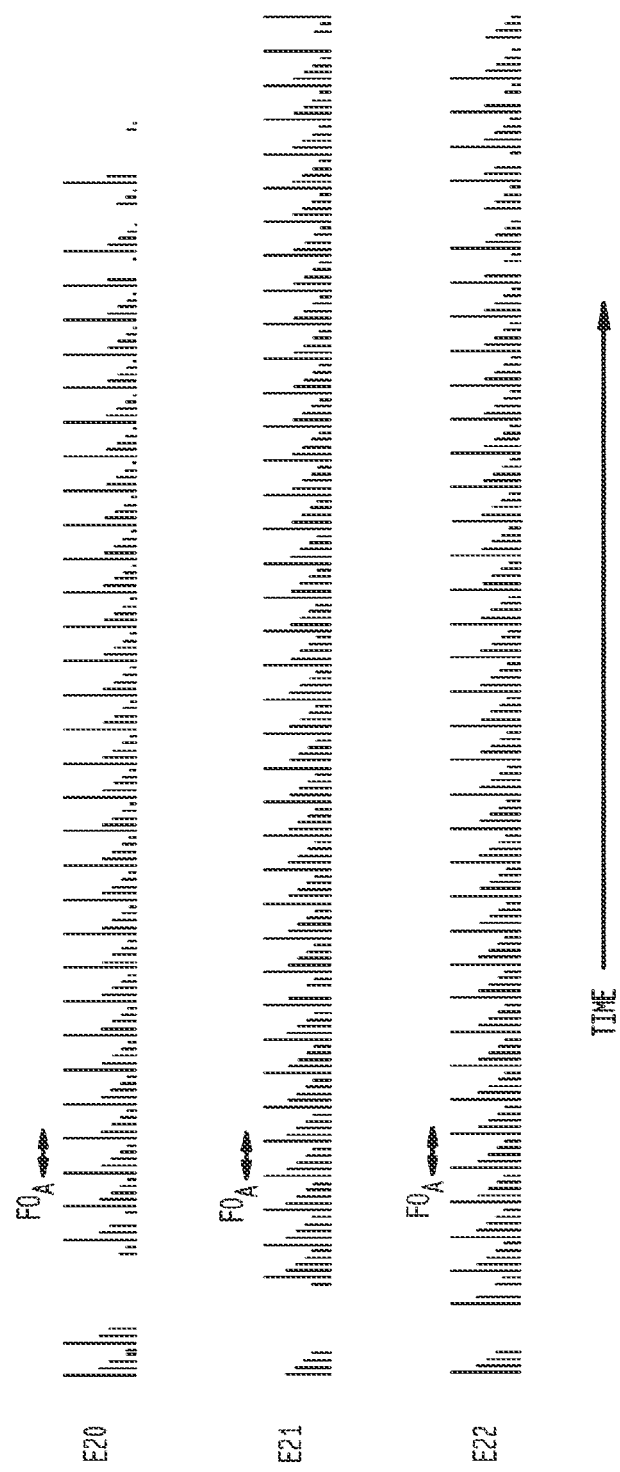
FIG. 9 is an electrodogram illustrating three sequences of fixed rate stimulation pulses modulated using a single extracted fundamental frequency.
Figure 10:
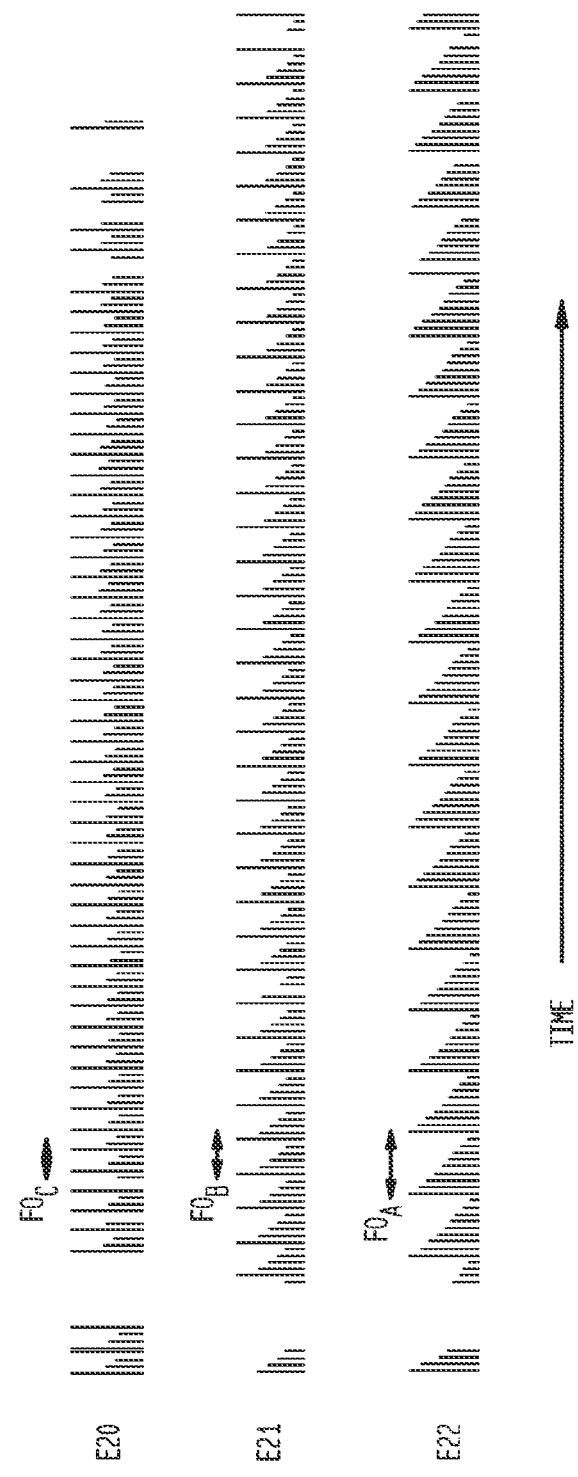
FIG. 10 is an electrodogram illustrating three sequences of fixed rate stimulation pulses modulated using three different extracted fundamental frequencies.

In summary, FIGS. 3 and 4 illustrate techniques that improve a recipient's perception of simultaneously received multiple frequencies (e.g., multiple F0s) included with sound signals. In particular, the techniques presented herein identify and track multiple sound sources, extract one or more frequencies of each sound source, and, in certain embodiments enable multiple frequencies to be used to amplitude modulation stimulation pulses delivered via different stimulation channels. FIGS. 8, 9, and 10 illustrate further details regarding pitch encoding via amplitude modulations. For ease of illustration, FIGS. 8, 9, and 10 are described with reference to the arrangement of FIG. 3.

More specifically, referring first to FIG. 8, shown is an electrodogram illustrating sequences of fixed rate stimulation pulses delivered across three stimulation channels, identified as electrode 20 (E20), electrode 21 (E21), and electrode 22 (E22). In FIG. 8, the stimulation pulses are each represented by the vertical lines and are determined using only modules 334, 336, 338, and 340 of FIG. 3. In these examples, the stimulation pulse determination module 340 amplitude modulates the stimulation pulse sequences based only on the channel envelopes that are output by the envelope extraction module 336. Each of the three stimulation channels E20, E21, and E22 are modulated in substantially the same manner. Moreover, these pulses in FIG. 8 are generated using monopolar stimulation because the signal is not passed through the channel focusing control module 350.

Referring next to FIG. 9, shown is an electrodogram illustrating sequences of fixed rate stimulation pulses delivered across three stimulation channels, identified as electrode 20 (E20), electrode 21 (E21), and electrode 22 (E22). In FIG. 9, the stimulation pulses are each represented by the vertical lines and, in these examples, the sound signals are passed through the fundamental frequency module 342, the periodic probability estimator module 346, and channel modulation module 348. In stimulation pulse determination module 340, the pulse sequences are amplitude modulated by the modified channel envelopes that are the outputs of the channel modulation module 348. Additionally, in this example only one source, with a fundamental frequency of $F0_A$, is used to modulate the channel envelopes and, as such, each of the three stimulation channels E20, E21, and E22 are modulated in substantially the same manner (i.e., using fundamental frequency $F0_A$). The stimulation pulses in FIG. 9 may be generated using varying degrees of focusing between monopolar stimulation and focused stimulation because the signal is passed through the channel focusing control module 350.

Referring next to FIG. 10, shown is an electrodogram illustrating sequences of fixed rate pulses delivered across three stimulation channels, identified as electrode 20 (E20), electrode 21 (E21), and electrode 22 (E22). In FIG. 10, the stimulation pulses are each represented by the vertical lines and, in these examples, the sound signals are passed through the fundamental frequency module 342, the periodic probability estimator module 346, and channel modulation module 348. In stimulation pulse determination module 340, the pulse sequences are amplitude modulated by the modified channel envelopes that are the outputs of the channel modulation module 348. In this example, three different sources are used to modulate the channel envelopes. More specifically, the first source has a fundamental frequency of $F0_A$, the second source has a fundamental frequency of $F0_B$, and the third source has a fundamental frequency of $F0_C$. As such, as shown in FIG. 10, the stimulation pulses delivered at E22 are modulated using $F0_A$, the stimulation pulses delivered at E21 are modulated using $F0_B$, and the stimulation pulses delivered at E20 are modulated using $F0_C$. The stimulation pulses in FIG. 10 may be generated using varying degrees of focusing between monopolar stimulation and focused stimulation because the signal is passed through the channel focusing control module 350.

Figure 11:
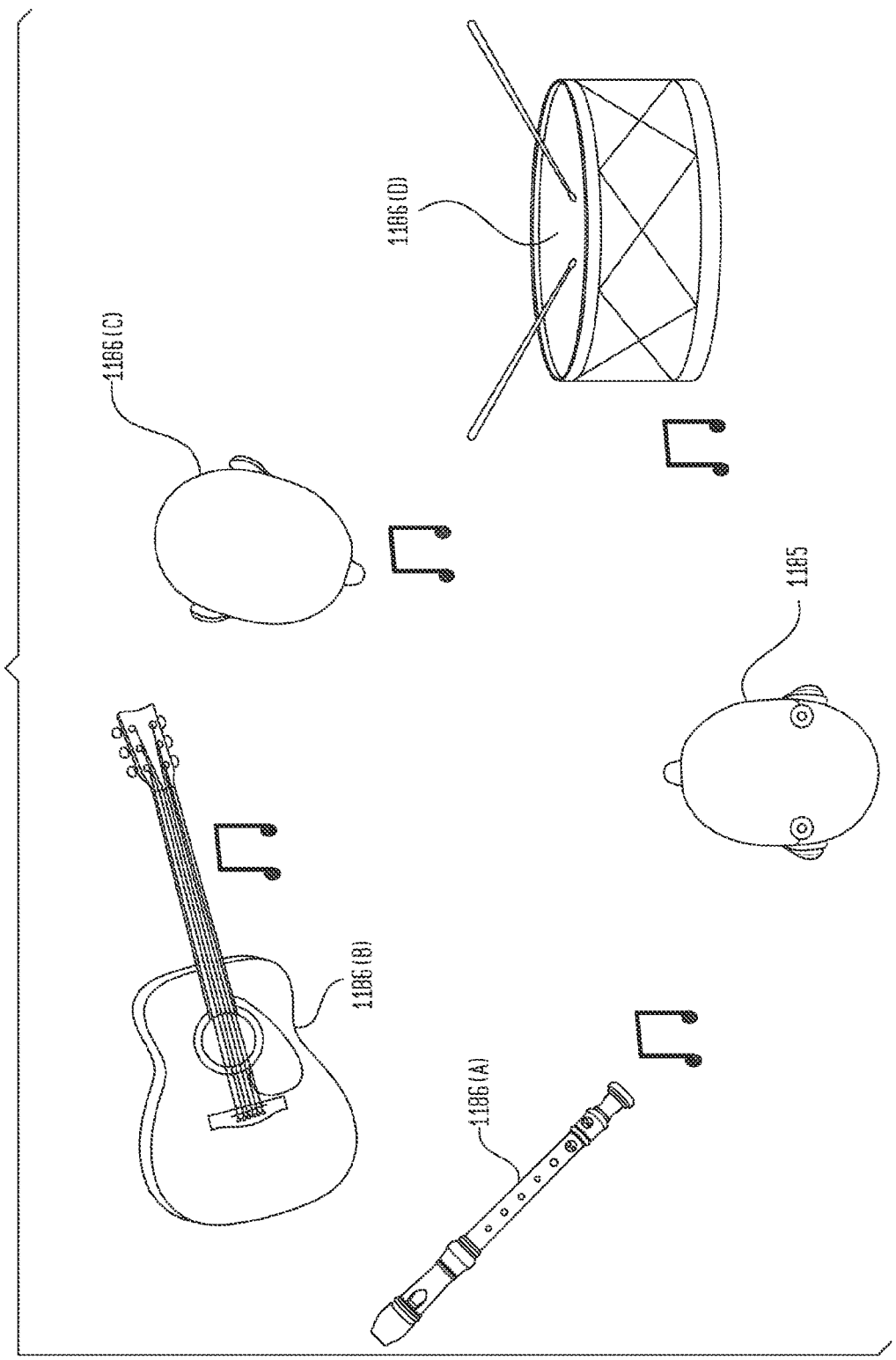
FIG. 11 illustrates an example scenario in which a hearing prosthesis receives sound signals that include multiple sound sources.
Figure 12:
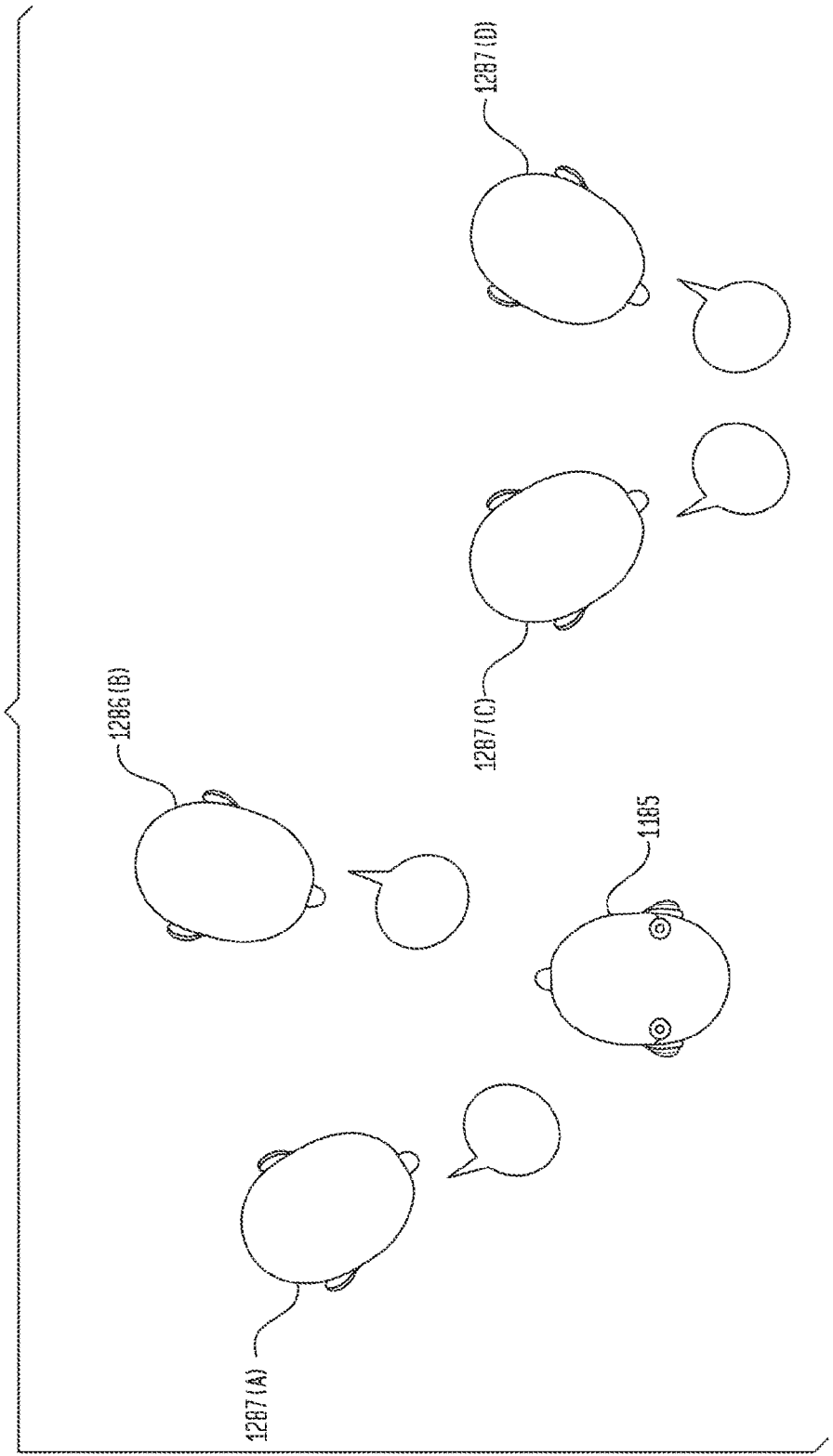
FIG. 12 illustrates another example scenario in which a hearing prosthesis receives sound signals that include multiple sound sources.

FIGS. 11 and 12 illustrate example scenarios with the sound environments include multiple sound sources and, as such, in which the techniques presented herein may be implemented to improve the perception of multiple frequencies, such as multiple F0s. In FIG. 11, a hearing prosthesis recipient 1185 is listening to music signals that are comprises of (include) four different sound sources, namely: recorder 1186(A), guitar 1186(B), vocalist 1186(C), and drum 1186(D). In FIG. 12, the recipient 1185 is having a conversation with Speaker/Talker 1287(A) and Talker 1287(B). Meanwhile, Talkers 1287(C) and 1287(D) are holding a separate conversation nearby. These scenarios will be used in several examples below.

As noted, in each of the examples of FIGS. 11 and 12, there are several sound sources that simultaneously deliver sounds to the hearing prosthesis of recipient 1185 (e.g., multiple instruments being played simultaneously, multiple speakers, etc.) and, as described above, it is possible to extract the melody, beats, and fundamental frequency of individual components of the sound sources. For example, in certain embodiments, measurements relating to spectral attributes such as harmonicity, spectral smoothness, etc. may be used to extract the fundamental frequencies of the different sources. In other embodiments, non-negative matrix factorization (NMF) based methods, sparse coding based methods may be used to separate the sources and, potentially, extract the fundamental frequencies of the separated sources.

Also as described above, the techniques presented herein are able to encode the multiple frequencies in the stimulation signals delivered to the recipient 1185. For example, when a strong sense of pitch, or high harmonic probability, is detected for a sound, the techniques presented herein deliver deep modulations over the carrier pulses at the rate of one of the fundamental frequencies. The techniques presented herein are not restricted to a single F0 encoded across all channels, but instead multiple F0s, harmonics, etc. can be delivered across different channels, or groups of channels, as deep modulations.

Using the scenario in FIG. 11, the F0 from each source 1186(A)-1186(D) is tracked and extracted using the methods described above. Each F0 that is extracted from its source will then be used to modulate the signal(s) being delivered to one or more stimulation channels. Multiple concurrent F0s can be distributed across channels according to their relative strength in each frequency channel over time, with only a single F0 assigned to any given channel at any one time (e.g., based on periodic probability). In certain embodiments, the dominant source in a given frequency channel is used to select the F0 for that channel. In other embodiments, the available channels are split amongst the detected sources with a preference for coding each source in the channels based on the source with the most energy. In still other embodiments, when only one source is being encoded, a single F0 and one or more of its harmonics from the one musical instrument will be extracted and used to modulate one or more channels.

Using the scenario in FIG. 12, the F0 for each source, 1287(A) through 1287(D), will be tracked and extracted using the methods described above. Each F0 will then be used to modulate the signal being delivered to one channel or more channels. As before, multiple concurrent F0s are to be distributed across channels according to, for example, their relative strength in each frequency channel over time, with a single F0 assigned to any given channel at any one time.

Also as described above, to maximize pitch specificity with the techniques presented, the above encoding strategies may be used in combination with stimulation resolution adaption techniques, such as focused stimulation techniques. In contrast to monopolar stimulation, focused stimulation improves discrimination of spectral features and increases the temporal independence of different frequency channels. The combined effects of focused stimulation and the enhanced sound coding strategies described herein improve the ability of hearing prosthesis recipients to discriminate and follow multiple pitches over time.

Also as described, a feature of the techniques presented herein is that the different sources and/or frequencies provided can be controlled in a variety of ways. For example, in certain embodiments, bilateral control may be provided where different frequencies or sound sources may be delivered to different ears. For example, in the scenario of FIG. 11, the F0 from the recorder 1186(A) may be sent to one ear, and the F0 from the vocalist 1186(C) may be sent to the other ear. Alternatively, different harmonics from only one instrument may be separated and sent to different ears to reduce channel interactions. In another example described with reference to the scenario of FIG. 12, the F0 from Talker 1287(A) may be sent only to the left ear, and the F0 from Talker 1287(B) may be sent only to the right ear. This technique may improve perceptual segregation of different sources or pitches. Bilateral control may be done either manually by the user or may be automated (e.g., based on estimated spatial location in a real-world situation or in a recorded stereo sound file).

In further embodiments presented herein, source selection may be provided where the recipient is given the option to select a specific sound source. For example, in the scenario of FIG. 12, recipient 1285 may select Talker 1186(B) and the F0 therefrom can be used to provide deep modulations across all channels until the desired source is changed to a different talker. Users may change sources using a "next" button on an external component, a remote control, a personal audio device, etc. to cycle through different sources. In another example described with reference to the scenario of FIG. 11, the recipient 1185 is provided with a graphical display of the spatial arrangement of the different sound sources, and the user is able to select the desired source using on the graphical display.

In still further embodiments, the techniques presented herein may provide the recipient 1185 with the option to modify the relative volume of different pitches or sources, such as by changing the volume of different instruments in a musical mix. For example, in the arrangement of FIG. 11, the recipient 1185 may wish to increase the vocals 1186(C) and the drum 1186(D) relative to the other instruments. For a single musical instrument, the recipient 1185 may change the balance between the F0 and other harmonics to modify the timbre. In another example described with reference to FIG. 12, recipient 1185 may choose to increase the volume of Talker 1187(B), who is slightly farther away than Talker 1187(A). Recipient 1185 may also choose to decrease the volume of Talkers 1187(C) and 1187(D) or to mute their sources entirely. Volume modification may be done manually using an external component, a remote control, a personal audio device, graphical display, etc.

Figure 13:
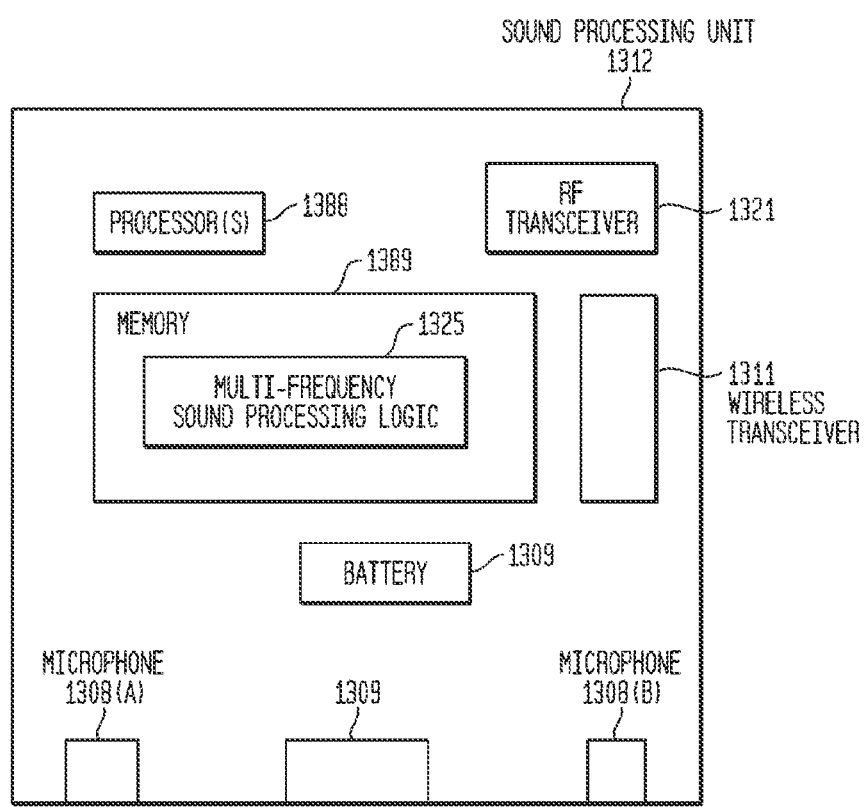
FIG. 13 is a block diagram of a sound processing unit in accordance with embodiments presented herein.

FIG. 13 is a schematic block diagram illustrating an arrangement for a sound processing unit in accordance with an embodiment of the present invention. For ease of description, the sound processing unit of FIG. 13 is referred to as sound processing unit 1312.

As shown, the sound processing unit 1312 includes one or more processors 1388 and a memory 1389. The memory 1389 includes multi-frequency sound processing logic 1325. Sound processing unit 1312 also comprises two microphones 1308(A) and 1308(B), one or more auxiliary input devices 1309 (e.g., audio ports, such as a Direct Audio Input (DAI), data ports, such as a Universal Serial Bus (USB) port, cable port, etc.), a wireless transmitter/receiver (transceiver) 1311, a radio-frequency (RF) transceiver 1321, and at least one battery 1307.

The memory 1389 may be read only memory (ROM), random access memory (RAM), or another type of physical/tangible memory storage device. Thus, in general, the memory 1389 may comprise one or more tangible (non-transitory) computer readable storage media (e.g., a memory device) encoded with software comprising computer executable instructions and when the software, multi-frequency sound processing logic 1325, is executed by the one or more processors 1388, it is operable to perform the operations described herein with reference to a multi-frequency sound processor, as described elsewhere herein.

FIG. 13 illustrates software implementations for a multi-frequency sound processor. However, it is to be appreciated that one or more operations associated with the multi-frequency sound processor may be partially or fully implemented with digital logic gates in one or more application-specific integrated circuits (ASICs).

FIG. 14 is a flowchart illustrating a method 1400 in accordance with embodiments presented herein. Method 1400 begins at 1402 where a hearing prosthesis receives sound signals. At 1404, a plurality of frequencies are extracted from the sound signals and, at 1406, the sound signals are filtered to generate channelized sound signals. At 1408, a plurality of stimulation pulse sequences are determined, where each stimulation pulse sequences corresponds to one of the channelized sound signals. At 1410, each of the plurality of stimulation pulse sequences are amplitude modulated with one of the plurality of frequencies extracted from the sound signals. At least two of the plurality of stimulation pulse sequences are amplitude modulated with different ones of the plurality of frequencies extracted from the sound signals. At 1412, each of the plurality of stimulation pulse sequences are delivered to the recipient via one or more stimulation channels of the hearing prosthesis.

FIG. 15 is a flowchart illustrating a method 1500 in accordance with embodiments presented herein. Method 1500 begins at 1502 where a hearing prosthesis receives sound signals. At 1504, at least one frequency is extracted from the sound signals and, at 1506, the sound signals are filtered to generate channelized sound signals. At 1508, a plurality of stimulation pulse sequences are determined, where each of the plurality of stimulation pulse sequences corresponds to one of the channelized sound signals. At 1510, a periodic probability is determined for each of a plurality of the channelized sound signals, where a periodic probability indicates a degree of association between a channelized sound signal and the at least one frequency extracted from the sound signals. At 1512, at least one of the plurality of stimulation pulse sequences is amplitude modulated based on a periodic probability associating a channelized sound signal corresponding to the at least one stimulation pulse sequence and the at least one frequency extracted from the sound signals.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
receiving sound signals at a hearing device;
extracting a fundamental frequency of at least one sound source associated with the sound signals;
extracting at least one harmonic of the fundamental frequency of at least one sound source associated with the sound signals;
determining a plurality of stimulation pulse sequences based on the sound signals;
amplitude modulating at least a first one of the plurality of stimulation pulse sequences with the fundamental frequency of the at least one sound source; and
amplitude modulating at least a second of the plurality of stimulation pulse sequences with the at least one harmonic of the fundamental frequency.

2. The method of claim 1, further comprising:
delivering each of the plurality of stimulation pulse sequences to a recipient of the hearing device via one or more stimulation channels of the hearing device.

3. The method of claim 1, further comprising:
filtering the sound signals to generate channelized sound signals,
wherein each of the plurality of stimulation pulse sequences corresponds to one of the channelized sound signals.

4. The method of claim 3, further comprising:
determining a periodic probability for each of a plurality of the channelized sound signals, wherein the periodic probability indicates a degree of association between a channelized sound signal and either the fundamental frequency of the at least one sound source or the at least one harmonic of the fundamental frequency.

5. The method of claim 4, further comprising:
setting a stimulus resolution of at least one of the plurality of stimulation pulse sequences based on the periodic probability determined for a channelized sound signal corresponding to the at least one of the plurality of stimulation pulse sequences indicating association with either the fundamental frequency of the at least one sound source or the at least one harmonic of the fundamental frequency.

6. The method of claim 5, wherein setting a stimulus resolution of the at least one of the plurality of stimulation pulse sequences comprises:
setting a spatial resolution of the at least one of the plurality of stimulation pulse sequences based on the periodic probability determined for the corresponding channelized sound signal.

7. The method of claim 3, further comprising:
determining a periodic probability for each of a plurality of the channelized sound signals, wherein the periodic probability indicates a degree of association between a channelized sound signal and either the fundamental frequency of the at least one sound source or the at least one harmonic of the fundamental frequency,
wherein an amplitude modulation applied to at least one stimulation pulse sequence is based on the periodic probability determined for the channelized sound signal corresponding to the at least one stimulation pulse sequence indicating association with either the fundamental frequency of the at least one sound source or the at least one harmonic of the fundamental frequency.

8. The method of claim 1, further comprising:
receiving an input from a user; and
determining an amplitude modulation applied to at least one of the plurality of stimulation pulse sequences at least partially based on the input from the user.

9. The method of claim 1, further comprising:
determining a sound class of the sound signals,
amplitude modulating one or more of the at least a first one of the plurality of stimulation pulse sequences or the second of the plurality of stimulation pulse sequences dependent upon on the sound class of the sound signals.

10. The method of claim 9, wherein the sound signals can be classified into a plurality of sound classes, and wherein amplitude modulating one or more of the at least a first one of the plurality of stimulation pulse sequences or the second of the plurality of stimulation pulse sequences dependent upon on the sound class of the sound signals comprises:
determining whether the sound class of the sound signals matches a selected subset of the plurality of sound classes;
only amplitude modulating the one or more of the plurality of stimulation pulse sequences when the sound class of the sound signals matches a sound class from the selected subset of the plurality of sound classes.

11. A device, comprising:
one or more sound input elements configured to receive sound signals;
a memory;
a stimulator unit; and
one or more processors configured to:
extract a fundamental frequency of at least one sound source associated with the sound signals,
extract at least one harmonic of the fundamental frequency of at least one sound source associated with the sound signals,
determine a plurality of stimulation pulse sequences based on the sound signals,
determine an amplitude modulation for at least a first one of the plurality of stimulation pulse sequences with the fundamental frequency of the at least one sound source, and
determine an amplitude modulation for at least a second of the plurality of stimulation pulse sequences with the at least one harmonic of the fundamental frequency.

12. The device of claim 11, wherein the stimulator unit is configured to:
deliver each of the plurality of stimulation pulse sequences, with corresponding determined amplitude modulations, to a recipient of the device via one or more stimulation channels of the device.

13. The device of claim 11, wherein the one or more processors are configured to:
filter the sound signals to generate channelized sound signals,
wherein each of the plurality of stimulation pulse sequences corresponds to one of the channelized sound signals.

14. The device of claim 13, wherein the one or more processors are configured to:
determine a periodic probability for each of a plurality of the channelized sound signals, wherein the periodic probability indicates a degree of association between a channelized sound signal and either the fundamental frequency of the at least one sound source or the at least one harmonic of the fundamental frequency.

15. The device of claim 14, wherein the one or more processors are configured to:
set a stimulus resolution of at least one of the plurality of stimulation pulse sequences based on the periodic probability determined for a channelized sound signal corresponding to the at least one of the plurality of stimulation pulse sequences indicating association with either the fundamental frequency of the at least one sound source or the at least one harmonic of the fundamental frequency.

16. The device of claim 15, wherein to set a stimulus resolution of the at least one of the plurality of stimulation pulse sequences, the one or more processors are configured to:
set a spatial resolution of the at least one of the plurality of stimulation pulse sequences based on the periodic probability determined for the corresponding channelized sound signal.

17. The device of claim 13, wherein the one or more processors are configured to:
determine a periodic probability for each of a plurality of the channelized sound signals, wherein the periodic probability indicates a degree of association between a channelized sound signal and either the fundamental frequency of the at least one sound source or the at least one harmonic of the fundamental frequency,
wherein an amplitude modulation determined for at least one stimulation pulse sequence is based on the periodic probability determined for a channelized sound signal corresponding to the at least one stimulation pulse sequence indicating association with either the fundamental frequency of the at least one sound source or the at least one harmonic of the fundamental frequency.

18. The device of claim 11, wherein the one or more processors are configured to:
obtain an input from a user; and determine an amplitude modulation applied to at least one of the plurality of stimulation pulse sequences at least partially based on the input from the user.

19. The device of claim 11, wherein the one or more processors are configured to:
   determine a sound class of the sound signals,
   determine an amplitude modulation for one or more of the at least a first one of the plurality of stimulation pulse sequences or the second of the plurality of stimulation pulse sequences dependent upon on the sound class of the sound signals.

20. The device of claim 19, wherein the sound signals can be classified into a plurality of sound classes, and wherein to determine an amplitude modulation for one or more of the at least a first one of the plurality of stimulation pulse sequences or the second of the plurality of stimulation pulse sequences dependent upon on the sound class of the sound signals, the one or more processors are configured to:
   determine whether the sound class of the sound signals matches a selected subset of the plurality of sound classes;
   only determine an amplitude modulation for the one or more of the plurality of stimulation pulse sequences when the sound class of the sound signals matches a sound class from the selected subset of the plurality of sound classes.

* * * * *